(12) United States Patent
Lee et al.

(10) Patent No.: US 7,504,380 B2
(45) Date of Patent: Mar. 17, 2009

(54) ANTIMICROBIAL PEPTIDE ISOLATED FROM HALOCYNTHIA AURANTIUM

(75) Inventors: In-Hee Lee, Choongchungnam-do (KR); Seok-Min Son, Choongchungnam-do (KR); Woong-Sik Jang, Choongchungnam-do (KR); Kyu-Nam Kim, Kyunggi-do (KR)

(73) Assignee: Industry-Academic Cooperation Foundation, Hoseo University, Seoul (KR)

( * ) Notice: Subject to any disclaimer, the term of this patent is extended or adjusted under 35 U.S.C. 154(b) by 239 days.

(21) Appl. No.: 10/535,624

(22) PCT Filed: Nov. 22, 2002

(86) PCT No.: PCT/KR02/02195

§ 371 (c)(1),
(2), (4) Date: Oct. 25, 2005

(87) PCT Pub. No.: WO2004/048407

PCT Pub. Date: Jun. 10, 2004

(65) Prior Publication Data

US 2006/0135748 A1    Jun. 22, 2006

(51) Int. Cl.
*A61K 38/03*    (2006.01)
(52) U.S. Cl. .............................. 514/13; 530/326; 435/32
(58) Field of Classification Search ........................ None
See application file for complete search history.

(56) References Cited

FOREIGN PATENT DOCUMENTS

WO    WO 98/20028 A2    5/1998

OTHER PUBLICATIONS

Jang, et al., 2002, FEBS letters, 521, 81-86.*
Bellamy, W. et al., "Antibacterial spectrum of lactoferricin B, a potent bactericidal peptide derived from the N-terminal region of bovine lactoferrin," *J. Appl. Bacteriol.* 73:472-479, Blackwell Scientific Publications (1992).
Berridge, N.J., "Preparation of the Antibiotic Nisin," *Biochem. J.* 45:486-493, Portland Press (1949).
Blondelle, S.E., and Houghten, R.A., "Hemolytic and Antimicrobial Activities of the Twenty-Four Individual Omission Analogues of Melittin," *Biochemistry* 30:4671-4678, American Chemical Society (1991).
Casteels, P., et al., "Apidaecins: antibacterial peptides from honeybees," *EMBO J.* 8:2387-2391, Oxford University Press (1989).
Cociancich, S., et al., "Novel inducible antibacterial peptides from a hemipteran insect, the sap-sucking bug *Pyrrhocoris apterus*," *Biochem. J.* 300:567-575, Portland Press (1994).
Dimarcq, J.-L., et al., "Insect immunity: expression of the two major inducible antibacterial peptides, defensin and diptericin, in *Phormia terranovae*", *EMBO J.* 9:2507-2515, Oxford University Press (1990).

Frank, R.W., et al., "Amino Acid Sequences of Two Proline-rich Bactenecins," *J. Biol. Chem.* 265:18871-18874, The American Society for Biochemistry and Molecular Biology, Inc. (1990).
Frohm, M., et al., "The Expression of the Gene Coding for the Antibacterial Peptide LL-37 Is Induced in Human Keratinocytes during Inflammatory Disorders," *J. Biol. Chem.* 272:15258-15263, The American Society for Biochemistry and Molecular Biology, Inc. (1997).
Gallo, R.L., et al., "Identification of CRAMP, a Cathelin-related Antimicrobial Peptide Expressed in the Embryonic and Adult Mouse," *J. Biol. Chem.* 272:13088-13093, The American Society for Biochemistry and Molecular Biology, Inc. (1997).
Ganz, T., et al., "Defensins—Natural Peptide Antibiotics of Human Neutrophils," *J. Clin. Invest.* 76:1427-1435, The American Society for Clinical Investigation, Inc. (1985).
Gibson, B.W., et al., "Novel Petide Fragments Originating from PGL$^a$ and the Caerulein and Xenopsin Precursors from *Xenopus laevis*," *J. Biol. Chem.* 261:5341-5349, The American Society of Biological Chemists, Inc. (1986).
Khan, A.A., et al., "Recombinant Bactericidal/Permeability-Increasing Protein ($rBPI_{21}$) in Combination with Sulfadiazine Is Active against *Toxoplasma gondii*," *Antimicrob. Agents Chemother.* 43:758-762, American Society for Microbiology (1999).
Lamberty, M., et al., "Solution Structures of the Antifungal Heliomicin and a Selected Variant with both Antibacterial and Antifungal Activites," *Biochemistry* 40:11995-12003, American Chemical Society (Oct. 2001).
Lemaitre, B., et al., "A recessive mutation, immune deficiency (*imd*), defines two distinct control pathways in the *Drosophila* host defense," *Proc. Natl. Acad. Sci. USA* 92:9465-9469, National Academy of Sciences (1995).
Nakamura, T., et al., Tachyplesin, a Class of Antimicrobial Peptide from the Hemoytes of the Horseshoe Crab (*Tachypleus tridentatus*), *J. Biol. Chem.* 263:16709-16713, The American Society for Biochemistry and Molecular Biology, Inc. (1988).
Oppenheim, F.G., et al., "Histantins, a Novel Family of Histidine-rich Proteins in Human Parotid Secretion," *J. Biol. Chem.* 263:7472-7477, The American Society for Biochemistry and Molecular Biology, Inc. (1988).
Park, C.B., et al., "Structure—activity analysis of buforin II, a histone H2A-derived antimicrobial peptide: The proline hinge is responsible for the cell-penetrating ability of buforin II,"*Proc. Natl. Acad. Sci. USA* 97:8245-8250, Naitonal Academy of Sciences (2000).

(Continued)

*Primary Examiner*—Andrew D Kosar
*Assistant Examiner*—Satyanarayana Gudibande
(74) *Attorney, Agent, or Firm*—Sterne, Kessler, Goldstein & Fox PLLC

(57) ABSTRACT

The present invention relates to an antimicrobial peptide isolated from *Halocynthia aurantium*, more particularly, to an antimicrobial peptide isolated from the body fluid of *Halocynthia aurantium* and an antimicrobial agent comprising the same as an active ingredient. The antimicrobial peptide of the present invention shows excellent antimicrobial activity under strong acidic and basic environments. Moreover, it also shows strong antimicrobial activity against resistant bacteria. So, it can be used usefully as a natural antimicrobial agent.

13 Claims, 16 Drawing Sheets

OTHER PUBLICATIONS

Selested, M.E., et al., "Indolicidin, a Novel Bactericidal Tridecapeptide Amide from Neutrophilis," *J. Biol. Chem. 267*:4292-4295, The American Society for Biochemistry and Molecular Biology, Inc. (1992).

Steiner, H., et al., "Seqence and specificity of two antibacterial proteins involved in insect immunity," *Nature 292*:246-248, Macmillan Journals Ltd. (1981).

Yang, S.-T., et al., "Selective cytotoxicity following Arg-to-Lys substitution in tritrpticin adopting a unique amphipathic turn structure," *FEBS Lett. 540*:229-233, Elsevier Sceince B.V. (Apr. 2003).

Zasloff, M., "Magainins, a class of antimicrobial peptides from *Xenopus* skin: Isolation, characterization of two active forms, and partial cDNA sequence of a precursor," *Proc. Natl. Acad. Sci. USA 84*:5449-5453, National Academy of Sciences (1987).

Zhao, C., et al., "Identification of a new member of the protegrin family by cDNA cloning," *FEBs Lett. 346*:285-288, Federation of European Biochemical Societies (1994).

Azumi, K., et al., "Halocyamines: Novel Antimicrobial Tetraptide-like Substances Isolated from the Hemocytes of the Solitary Ascidian *Halocynthia roretzi*," *Biochem. 29*:159-165, American Chemical Society (1990).

Azumi, K., et al., "Inhibitory Effect of Halocyamine, an Antimicrobial Substance from Ascidian Hemocytes, on the Growth of Fish Viruses and Marine Bacteria," *Experientia. 46*:1066-1068, Birkhäuser Verlag (1990).

Bellm, L., et al., "Protegrins: New Antibiotics of Mammalian Origin," *Expert Opin. Investing. Drugs. 9*:1731-1742, Ashley Publications Ltd. (2000).

Falla, T., et al., "Mode of Action of the Antimicrobial Peptide Indolicidin," *J. Biol. Chem. 271*:19298-19303, The American Society for Biochemistry and Molecular Biology, Inc. (1996).

Fehlbaum, P. et al., "Structure-Activity Analysis of Thanatin, a 21-Residue Inducible Insect Defense Peptide with Sequence Homology to Frog Skin Antimicrobial Peptides," *Proc. Natl. Acad. Sci. USA. 93*:1221-1225, National Academy of Sciences (1996).

Goraya, J., et al., "Peptides with Antimicrobial Activity from Four Different Families Isolated from the Skins of the North American Frogs *Rana luteiventris, Rana berlandieri* and *Rana pipines*," *Eur. J. Biochem. 267*:894-900, Federation of European Biochemical Societies (2000).

Hancock, R.E., et al., "Cationic Bactericidal Peptides," *Adv. Microbial Physicol. 37*:135-175, Academic Press Inc. (1995).

Hancock, R.E., et al., "The Role of Antimicrobial Peptides in Animal Defenses," *Proc. Natl. Acad. Sci. USA. 97*:8856-8861, National Academy of Sciences (2000).

Hetru, C., et al., "Androctonin, A Hydrophilic Disulphide-Bridged Non-Haemolytic Anti-Microbial Peptide: A Plausible Mode of Action," *Biochem. J. 345*:653-664, Portland Press Ltd. (2000).

Iwanaga, S., et al., "New Types of Clotting Factors and Defense Molecules Found in Horseshoe Crab Hemolymph: Their Structures and Functions," *J. Biochem. 123*:1-15, The Japanese Biochemical Society (1998).

Jang, W.S., et al., "Halocidin: A New Antimicrobial Peptide from Hemocytes of the Solitary Tunicate, *Halocynthia Aurantium*," *FEBS Lett. 521*:81-86, Elsevier Science B.V. (May 2002).

Krause, A., et al., "LEAP-1, A Novel Highly Disulfide-Bonded Human Peptide, Exhibits Antimicrobial Activity," *FEBS Lett. 480*:147-150, Elsevier Science B.V. (2000).

Lee, I. H., et al., "Styelins, Broad-Spectrum Antimicrobial Peptides from the Solitary Tunicate, *Styela clava*," *Comp. Biochem. Physiol. B Biochem. Mol. Biol. 118B*:515-521, Elsevier Science Inc. (1997).

Lee, I. H., et al., "Clavanins, ά-helical Antimicrobial Peptides from Tunicate Hemocytes," *FEBS Lett. 400*:158-162, Elsevier Science B.V. (1997).

Lee, I. H., et al., "Effects of pH and Salinity on the Antimicrobial Properties of Clavanins,"*Infection and Immunity. 65*:2898-2903, American Society for Microbilogy (1997).

Lee, I. H., et al., "Dicynthaurin: An Antimicrobial Peptide from Hemocytes of the Solitary Tunicate, *Halocynthia aurantium*," *Biochim. Biophys. Acta. 1527*:141-148, Elsevier Science B.V. (May 2001).

Lehrer, R. I., et al., "Defensins: Antimicrobial and Cytotoxic Peptides of Mammalian Cells," *Annu. Rev. Immunol. 11*:105-128, Annual Reviews Inc. (1993).

O'Neil, D. A., et al., "Expression and Regulation of the Human β-Defensins hBD-1 and hBD-2 in Intestinal Epithelium," *J. Immunol. 163*:6718-6724, The American Association of Immunologists (1999).

Piers, K. L., et al., "Improvement of Outer Membrane-Permeabilizing and Lipopolysaccharide-Binding Activities of an Antimicrobial Cationic Peptide by C-Terminal Modification," *Antimicrob. Agents Chemother. 38*:2311-2316, The American Society for Microbiology (1994).

Romeo, D., et al., "Structure and Bactericidal Activity of an Antibiotic Dodecapeptide Purified from Bovine Neutrophils," *J. Biol. Chem. 263*:9573-9575, The American Society for Biochemistry and Molecular Biology (1988).

Taylor, S. W., et al., "Styelin D, an Extensively Modifies Antimicrobial Peptide from Ascidian Hemocytes," *J. Biol. Chem. 275*:38417-38426, The American Society for Biochemistry and Molecular Biology (2000).

Zhang, L., et al., "Interaction of Cationic Antimicrobial Peptides with Model Membranes,"*J. Biol. Chem. 276*:35714-35722, The American Society for Biochemistry and Molecular Biology, Inc. (Jul. 2001).

Zhao, C., et al., "cDNA Cloning of Clavanins: Antimicrobial Peptides of Tunicate Hemocytes," *FEBS Lett. 410*:490-492, Elsevier Science B.V. (1997).

Zhao, C., et al., "cDNA Cloning of Three Cecropin-Like Antimicrobial Peptides (Styelins) from the Tunicate, *Styela clava*," *FEBS Lett. 412*:144-148, Elsevier Science B.V. (1997).

\* cited by examiner

18Hc  WLNALLHHGLNCAKGVLA natural 15Hc  ALLHHGLNCAKGVLA

FIG. 6
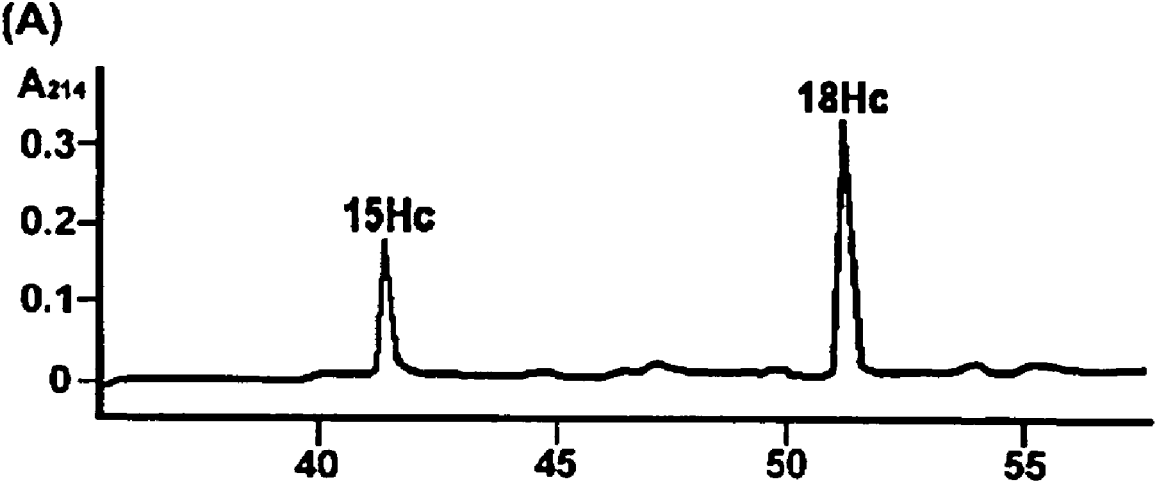
(A)
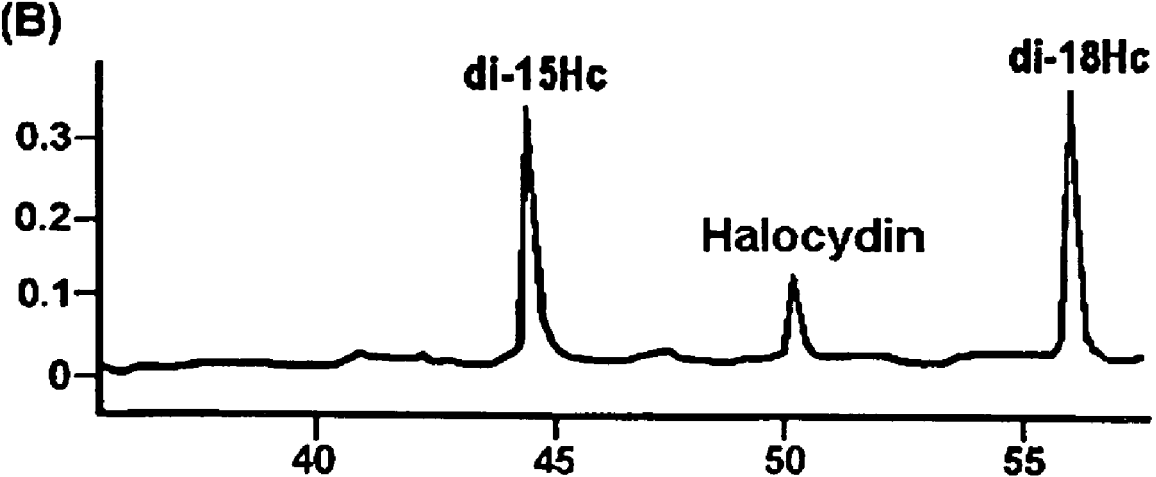
(B)
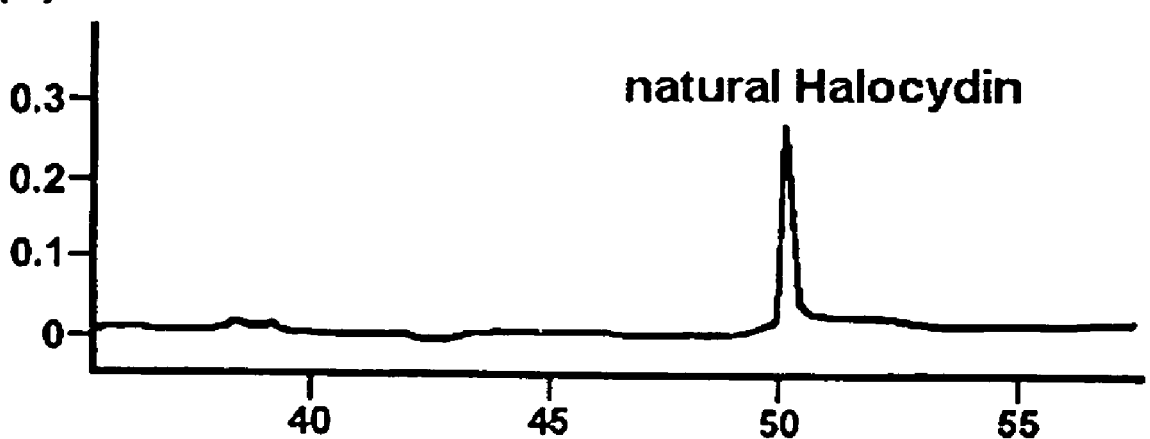
(C)

FIG. 7
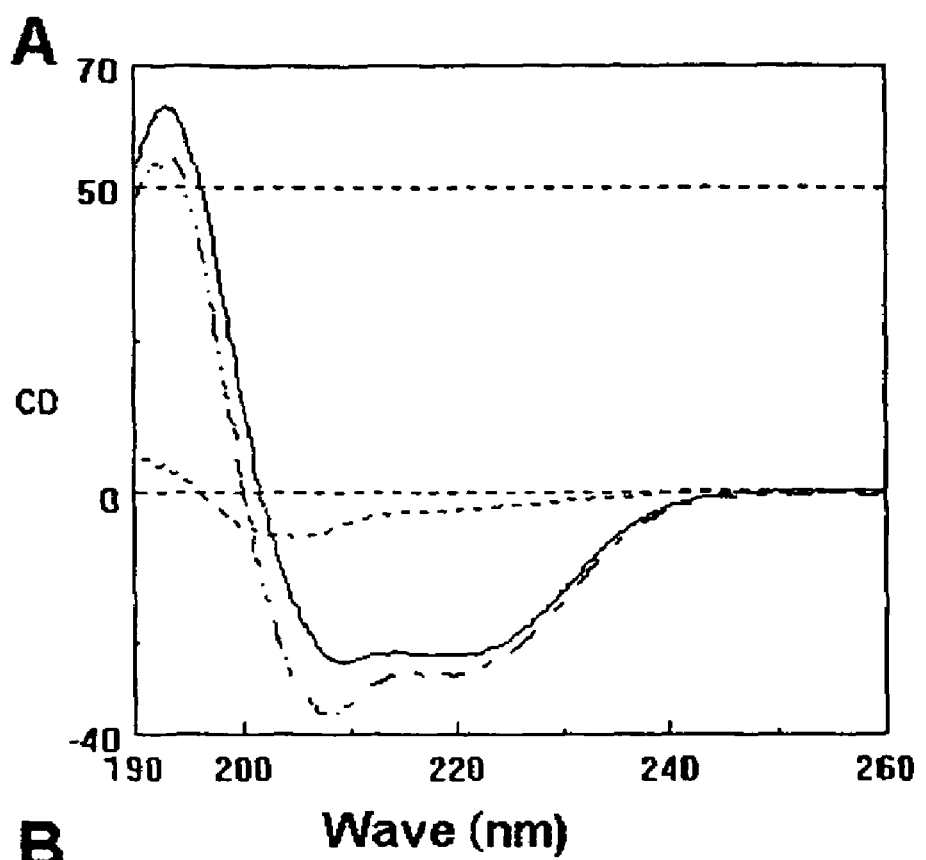
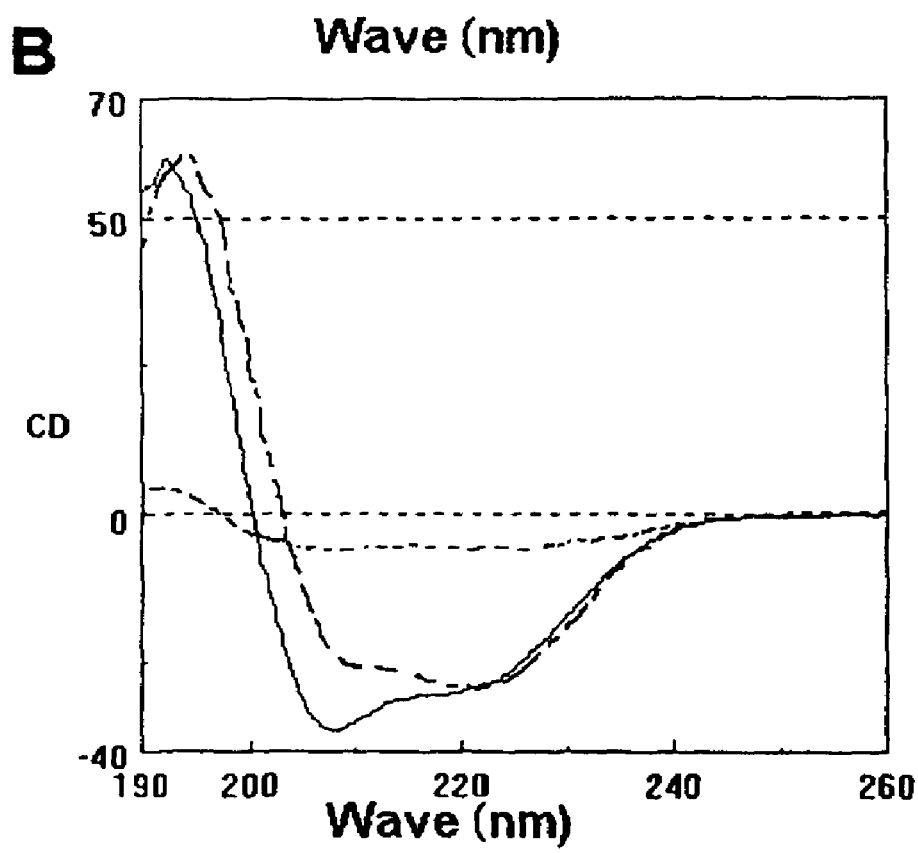

right axis: Peptide concentration(ug/ml), left axis: antimicrobial altivity(%)

right axis: Peptide concentration(ug/ml)
left axis: antimicrobial altivity(%)

right axis: Peptide concentration(ug/ml)
left axis: antimicrobial altivity(%)

FIG. 16
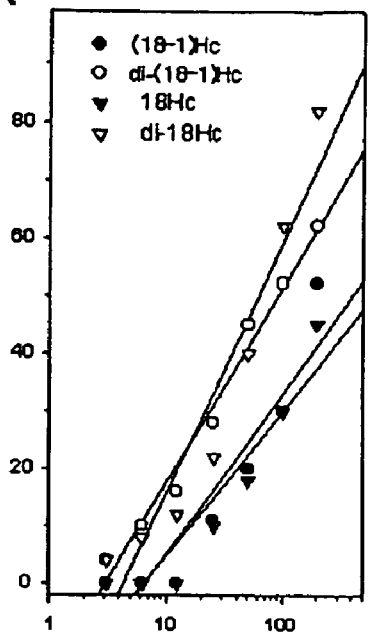
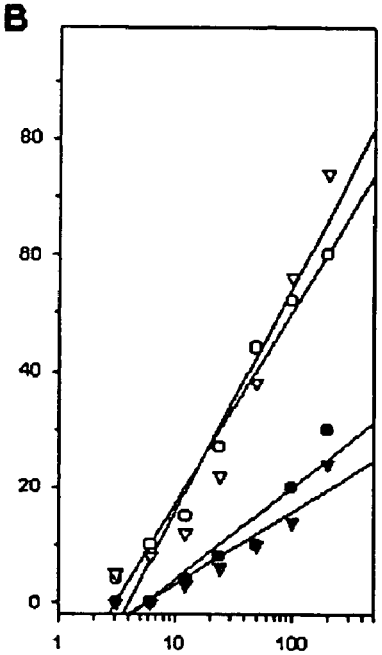
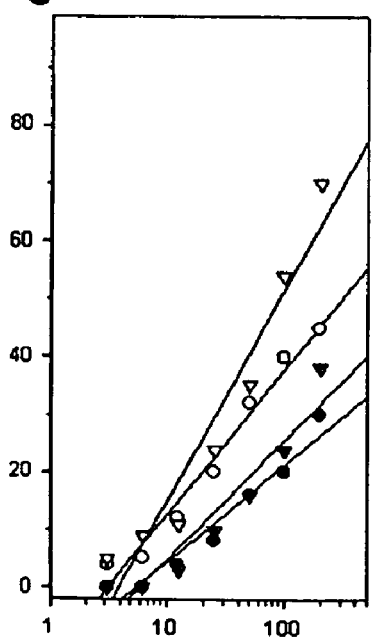
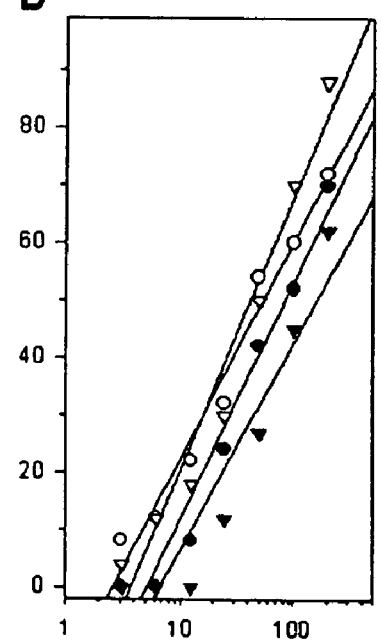
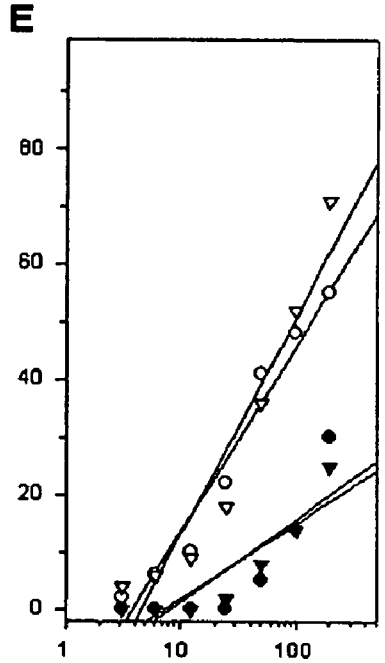
right axis: Peptide concentration(ug/ml), left axis: antimicrobial altivity(%)

SEQUENCE LISTING

```
<160> NUMBER OF SEQ ID NOS: 10

<210> SEQ ID NO 1
<211> LENGTH: 18
<212> TYPE: PRT
<213> ORGANISM: Halocynthia aurantium
<220> FEATURE:
<221> NAME/KEY: PEPTIDE
<222> LOCATION: (1)..(1)
<223> OTHER INFORMATION: 18mer of halocydin

<400> SEQUENCE: 1

Trp Leu Asn Ala Leu Leu His His Gly Leu Asn Cys Ala Lys Gly Val
1               5                   10                  15

Leu Ala

<210> SEQ ID NO 2
<211> LENGTH: 15
<212> TYPE: PRT
<213> ORGANISM: Halocynthia aurantium
<220> FEATURE:
<221> NAME/KEY: PEPTIDE
<222> LOCATION: (1)..(1)
<223> OTHER INFORMATION: 15mer of halocydin

<400> SEQUENCE: 2

Trp Leu Asn Ala Leu Leu His His Gly Leu Asn Cys Ala Lys Gly
1               5                   10                  15

<210> SEQ ID NO 3
<211> LENGTH: 17
<212> TYPE: PRT
<213> ORGANISM: Halocynthia aurantium
<220> FEATURE:
<221> NAME/KEY: PEPTIDE
<222> LOCATION: (1)..(17)
<223> OTHER INFORMATION: 17mer of halocydin

<400> SEQUENCE: 3

Trp Leu Asn Ala Leu Leu His His Gly Leu Asn Cys Ala Lys Gly Val
1               5                   10                  15

Leu

<210> SEQ ID NO 4
<211> LENGTH: 16
<212> TYPE: PRT
```

<213> ORGANISM: Halocynthia aurantium
<220> FEATURE:
<221> NAME/KEY: PEPTIDE
<222> LOCATION: (1)..(16)
<223> OTHER INFORMATION: 16mer of halocydin

<400> SEQUENCE: 4

Trp Leu Asn Ala Leu Leu His His Gly Leu Asn Cys Ala Lys Gly Val
1               5                   10                  15

<210> SEQ ID NO 5
<211> LENGTH: 14
<212> TYPE: PRT
<213> ORGANISM: Halocynthia aurantium
<220> FEATURE:
<221> NAME/KEY: PEPTIDE
<222> LOCATION: (1)..(14)
<223> OTHER INFORMATION: 14mer of halocydin

<400> SEQUENCE: 5

Trp Leu Asn Ala Leu Leu His His Gly Leu Asn Cys Ala Lys
1               5                   10

<210> SEQ ID NO 6
<211> LENGTH: 13
<212> TYPE: PRT
<213> ORGANISM: Halocynthia aurantium
<220> FEATURE:
<221> NAME/KEY: PEPTIDE
<222> LOCATION: (1)..(13)
<223> OTHER INFORMATION: 13mer of halocydin

<400> SEQUENCE: 6

Trp Leu Asn Ala Leu Leu His His Gly Leu Asn Cys Ala
1               5                   10

<210> SEQ ID NO 7
<211> LENGTH: 12
<212> TYPE: PRT
<213> ORGANISM: Halocynthia aurantium
<220> FEATURE:
<221> NAME/KEY: PEPTIDE
<222> LOCATION: (1)..(12)
<223> OTHER INFORMATION: 12mer of halocydin

<400> SEQUENCE: 7

Trp Leu Asn Ala Leu Leu His His Gly Leu Asn Cys
1               5                   10

<210> SEQ ID NO 8
<211> LENGTH: 18
<212> TYPE: PRT
<213> ORGANISM: Halocynthia aurantium
<220> FEATURE:
<221> NAME/KEY: PEPTIDE
<222> LOCATION: (1)..(18)
<223> OTHER INFORMATION: 18mer congener of halocydin

<400> SEQUENCE: 8

Trp Leu Asn Ala Leu Leu Lys Lys Gly Leu Asn Cys Ala Lys Gly Val
1               5                   10                  15

Leu Ala

<210> SEQ ID NO 9
<211> LENGTH: 19
<212> TYPE: PRT
<213> ORGANISM: Halocynthia aurantium
<220> FEATURE:

-continued

```
<221> NAME/KEY: PEPTIDE
<222> LOCATION: (1)..(19)
<223> OTHER INFORMATION: 19mer of halocydin

<400> SEQUENCE: 9

Lys Trp Leu Asn Ala Leu Leu His His Gly Leu Asn Cys Ala Lys Gly
1               5                   10                  15

Val Leu Ala

<210> SEQ ID NO 10
<211> LENGTH: 19
<212> TYPE: PRT
<213> ORGANISM: Halocynthia aurantium
<220> FEATURE:
<221> NAME/KEY: PEPTIDE
<222> LOCATION: (1)..(19)
<223> OTHER INFORMATION: 19mer congener of halocydin

<400> SEQUENCE: 10

Lys Trp Leu Asn Ala Leu Leu Lys Lys Gly Leu Asn Cys Ala Lys Gly
1               5                   10                  15

Val Leu Ala
```

ANTIMICROBIAL PEPTIDE ISOLATED FROM HALOCYNTHIA AURANTIUM

This application is the U.S. National Phase of International Application PCT/KR2002/002195, international filing date of Nov. 22, 2002.

REFERENCE TO A SEQUENCE LISTING SUBMITTED ELECTRONICALLY VIA EFS-WEB

This application includes a "SequenceListing.txt", 7,680 bytes, updated on Aug. 18, 2008, and submitted electronically via EFS-Web which is hereby incorporated by reference in its entirety. The submission of the sequence listing text file does not include any new matter.

FIELD OF THE INVENTION

The present invention relates to an antimicrobial peptide isolated from *Halocynthia aurantium*, more particularly, to an antimicrobial peptide isolated from the body fluid of *Halocynthia aurantium* and an antimicrobial agent comprising the same as an active ingredient. The antimicrobial peptide of the present invention shows excellent antimicrobial activity under strong acidic and basic environments. Moreover, it also shows strong antimicrobial activity against resistant bacteria. So, it can be used usefully as a natural antimicrobial agent.

BACKGROUND

Most researchers studying immunology have been interested rather in adaptive immunity having memory and specificity than in innate immunity, so far. Nevertheless, innate immunity plays an important role in self-defense system of animals. For instance, 1) innate immune cells prohibit the invasion of microorganisms through skin or epitherial cells of the intestines, 2) innate immune cells restrain pathogens invading into blood or body fluid with their phagocytosis, 3) innate immunity preferentially prevents various invading microorganisms from growing in body fluid after infection even before adaptive immunity or phagocytosis is activated since innate immunity does not have specificity. Cells that are responsible for innate immunity use various antimicrobial substances such as simple inorganic compounds ($H_2O_2$, NO, etc), antimicrobial peptides and proteins in order to function as the above. Antimicrobial peptides or proteins have been reported to be on mucosal epithelial surface, in body fluid and in intracellular organelles of phagocytes, and to have various sizes, structures and activity (Hancock, R. E. et al., *Proc. Natl. Acad. Sci.*, 2000, 97, 8856-8861). But there are common characteristics, too, that is, most antimicrobial peptides or proteins have complementary positive charge to negative charge of cell membrane of microorganisms, antimicrobial proteins having enzyme activity (proteases or muramidases) hydrolyze the membrane of bacteria and antimicrobial peptides also target in cell membrane of microorganisms (Zhang, L. et al., *J. Biol. Chem.*, 2001, 276, 35714-35722). Owing to these mechanisms, antimicrobial peptides are expected to be very helpful for the development of novel antibiotics that can be effectively used for the bacteria having resistance against conventional antibiotics. Frequent appearance of resistant strains resulted from overuse of chemical synthetic antibiotics evokes the interest in these antimicrobial peptides as well.

Antimicrobial peptides are largely classified two groups: one group is composed of peptides having bipolar α-helical structure and the other group is composed of peptides having β-sheet structure stabilized by intradisulfide bonds. Cysteine containing antimicrobial peptides mostly keep even number of cysteine residues from 2 to 8, which contribute to build intradisulfide bonds, resulting in the completion of a stable structure. Table 1 shows a classification of antimicrobial peptides having β-sheet structure by the number of cysteine residue in a molecule.

TABLE 1

β-sheet antimicrobial peptides classified by the number of intramolecular systeine

| Cysteine number | Peptide | Origin | Reference |
|---|---|---|---|
| 2 | Dodecapeptide | Ruminants | 1 |
|   | Thanatin | Insects | 2 |
|   | Bombinin | Amphibian | 3 |
| 4 | Tachyplesin | *Tachypleus tridentatus* | 4 |
|   | Androctonin | Scorpion | 5 |
|   | Protegrin | Pig | 6 |
| 6 | α-defensin | Leucocytes of mammalian | 7 |
|   | β-defensin | Epithelial cells of mammalian | 8 |
| 8 | Hepcidin | Human liver | 9 |

1. Romeo, D. et al., J. Biol. Chem., 1988, 263, 9573-9575.
2. Fehlbaum, P. et al., Proc, Natl, Acad, Sci., 1996, 93, 1221-1225.
3. Goraya, J. et al., Eur. J. Biochem., 2000, 267, 894-900.
4. Iwanaga, S. et al., J. Biochem., 1998, 123, 1-15.
5. Hetru, C. et al., Biochem. J., 2000, 345, 653-644.
6. Ganz, T. et al., Drugs, 2000, 9, 1731-1742.
7. Lehrer, R. I. et al., Annu. Rev. Immunol., 1993, 11, 105-128.
8. O'Neil, D. A. et al., J. Immunol., 1999, 163, 6718-6724.
9. Krause, A. et al., FEBS Lett., 2000, 480, 147-150.

Working mechanism and specificity of antimicrobial peptides depend on the way to work mutually with bacterial cell membranes. Generally, peptides are accepted through self-promoted uptake pathway by working with LPS (lipopolysaccharide) on the surface of Gram-negative bacteria. The first step of the accepting process is that the peptides are adhered to divalent cation-binding sites of LPS on cell surface, and the second step is that the peptides are inserted in cell membrane to form a channel.

In the first step, peptides can bind to LPS with 3 times as high affinity as divalent cations like $Mn^{++}$ or $Mg^{++}$, so that they can be substituted for the divalent cations, causing a break down of a general property of cell membrane, especially of outer membrane. Such affected bacterial cell membrane makes a gap temporarily, through which hydrophobic substances, low-molecular proteins or antibiotics can pass and especially peptides are inserted effectively (Piers, K. L. et al., *Antimicrob. Agents Chemother.*, 1994, 38, 2311-2316).

In the second step, peptides are inserted in cell membrane to form a channel, during which magnetism of cation peptides works with anions of bacterial membrane, so that hydrophobic region faces membrane and hydrophilic region faces inner side to form a channel (Hancock, R. E. et al., *Adv. Microbial Physiol.*, 1995, 37, 135-175). The channel is formed well when potential difference is big, the amount of anion lipids is great and the quantity of cholesterol is small. A well-formed channel causes a break down of membrane structure, resulting in the death of bacteria (Falla, T. et al., *J. Biol. Chem.*, 1996, 271, 19298-19303). On the contrary, eukaryotic cells containing a huge amount of cholesterol but a small quantity of anion lipid do not provide a good condition for the working of peptides. Thus, the peptides show a highly selective activity against bacteria. Based on the above reasons, antimicrobial peptides are noticed as novel antibiotics with less cytotoxicity. Besides, the advantages of antimicrobial peptides, as novel antibiotics, are as follows.

1. Preventing the appearance of resistant bacteria by destroying bacterial membrane physically.

2. Working faster than the life cycle of bacteria.

3. Working effectively on resistant bacteria having resistance against conventional antibiotics.

4. Having wide antimicrobial spectrum.

5. Having an anti-endotoxicity effect owing to the binding capacity to LPS, etc.

6. Being able to be mass-produced using genetic engineering techniques and developed as a novel medicine with a less production cost.

From the viewpoint of animal systematic taxonomy, a tunicate belonging to deuterostomia is a kind of invertebrates classified into protochordata with such characteristics as having notochord and dorsal tubular nerve cord during tadpole larva period. Thus, a tunicate can be classified in pre-vertebrata with respect to systematic evolutionistics. Owing to such taxonomical position, a tunicate has been regarded as a model animal to prove evolutional origin of animal immune system. Especially, the body cavity (hemocoel) of a tunicate was observed to have lots of phagocytes having similar forms and functions to granulocytes and macrophages found in circulatory system of vertebrata (Bone, Q., *The Origin of Chordates*, 1979, 2nd edn). Studies to detect out antimicrobial peptides from body fluid cells of a tunicate have been undergoing and clavanin (Lee, I. H. et al., *FEBS Lett.*, 1997, 400, 158-162; Lee, I. H. et al., *Infection and Immunity*, 1997, 65, 2898-2903; Zhao, C. et al., *FEBS Lett.*, 1997, 410, 490-492) and styelin (Lee, I. H. et al., *Comp. Biochem. Physiol. B Biochem. Mol. Biol.*, 1997, 118, 515-521; Zhao, C. et al., *FEBS Lett.*, 1997, 412, 144-148) separated from body fluid cells of *Styela clava* are the representative antimicrobial peptides found out so far.

Two kinds of tunicates inhabit in the country. One is *Halocynthia roretzi* inhabiting mainly in southwest seashores or raised artificially and the other is *Halocynthia aurantium*, also called "silky sea squirt", inhabiting only in Sokcho (Kangwon-Do, Korea) area of the east coast. The former has been studied in Japan many years and disclosed to have an antimicrobial substance in the shape of transformed peptide (tetrapeptide) like halocyamine (Azumi, K. et al., *Experientia*, 1990, 46, 1066-1068; K. Azumi et al., *Biochemistry*, 1990, 29, 159-165). But there is no report yet that an antimicrobial peptide is separated from the latter, *Halocynthia aurantium*.

Thus, the present inventors investigated if there is any antimicrobial peptide in body fluid cells of *Halocynthia aurantium*. As a result, the present inventors separated an antimicrobial peptide named as dicinthaurin (Lee, I. H. et al., *Biochem. Biophys. Acta*, 2001, in press), and further, separated another antimicrobial peptide recently. The present inventors have accomplished this invention by analyzing the structure of the newly separated antimicrobial peptide and confirming the excellent antimicrobial activity thereof.

DETAILED DESCRIPTION OF PREFERRED EMBODIMENTS

It is an object of the present invention to provide an antimicrobial peptide isolated from *Halocynthia aurantium* and an antimicrobial agent comprising the same as an active ingredient.

To achieve the above object, the present invention provides an antimicrobial peptide isolated from the body fluid of *Halocynthia aurantium* and an antimicrobial agent comprising the same as an active ingredient.

Hereinafter, the present invention is described in detail.

The present invention provides an antimicrobial peptide isolated from the body fluid of *Halocynthia aurantium*.

The antimicrobial peptide of the present invention is isolated from tunicate, wherein the tunicate is preferred to be *Halocynthia aurantium* called "silky sea squirt". However, it is a common knowledge for the people in this field that the antimicrobial peptide of the present invention is not limited thereto and can be isolated from other organisms or synthesized artificially.

The present invention provides a peptide represented by <Chemical Formula 1> having 18 amino acids represented by each figures.

$$W_1X_2B'_3U_4X_5X_6B_7B_8U_9X_{10}B'_{11}C_{12}U_{13}B_{14}U_{15}X_{16}X_{17}U_{18}$$
(SEQ ID NO:11). <Chemical Formula 1>

In the above <Chemical Formula 1>,

W represents tryptophane or its derivatives;

X ($X_2$, $X_5$, $X_6$, $X_{10}$, $X_{16}$ or $X_{17}$) represents more than one amino acid residue selected from a group consisting of tyrosine, valine, isoleucine, leucine, methionine, phenylalanine and tryptophane, and the derivatives thereof;

B ($X_7$, $X_8$ or $X_{14}$) represents more than one amino acid residue selected from a group consisting of arginine, lysine and histidine, and the derivatives thereof;

B' ($X_3$ or $X_{11}$) represents more than one amino acid residue selected from a group consisting of arginine, lysine and histidine or from a group consisting of asparagine and glutamine, and the derivatives thereof; and U ($X_4$, $X_9$, $X_{13}$, $X_{15}$ or $X_{18}$) represents more than one amino acid residue selected from a group consisting of glycine, serine, alanine and threonine, and the derivatives thereof.

As for the peptide of the present invention represented by the above <Chemical Formula 1>, it is preferable to select tryptophane for W, select one from a group consisting of leucine, isoleucine and valine for X, one from a group consisting of asparagine, glutamine, histidine, lysine and arginine for B, one from a group consisting of alanine, serine, and glycine for U, and select cysteine for C (SEQ ID NO: 12).

For building the peptide of the present invention represented by the above <Chemical Formula 1>, it is more preferable to select tryptophane for $W_1$, leucine for $X_2$, asparagine for $B'_3$, alanine for $U_4$, leucine for $X_5$, leucine for $X_6$, histidine for $B_7$, histidine for $B_8$, glycine for $U_9$, leucine for $X_{10}$, asparagine for $B'_{11}$, cysteine for $C_{12}$, alanine for $U_{13}$, lysine for $B_{14}$, glycine for $U_{15}$, valine for $X_{16}$, leucine for $X_{17}$ and alanine for $U_{18}$. Thus, it is most preferable for the peptide of the present invention to have amino acid sequence represented by SEQ. ID. No 1.

The present invention also provides a peptide having 15 amino acids represented by <Chemical Formula 2> in which three amino acids ($W_1X_2B'_3$) at N-terminal of the peptide represented by the above <Chemical Formula 1> are lost.

$$U_4X_5X_6B_7B_8U_9X_{10}B'_{11}C_{12}U_{13}B_{14}U_{15}X_{16}X_{17}U_{18}$$
(SEQ ID NO:13). <Chemical Formula 2>

In the above Formula,

X ($X_2$, $X_3$, $X_7$, $X_{13}$ or $X_{14}$) represents more than one amino acid residue selected from a group consisting of tyrosine, valine, isoleucine, leucine, methionine, phenylalanine and tryptophane, and the derivatives thereof;

B ($X_4$, $X_5$ or $X_{11}$) represents more than one amino acid residue selected from a group consisting of arginine, lysine and histidine, and the derivatives thereof;

B' ($X_8$) represents more than one amino acid residue selected from a group consisting of arginine, lysine and histidine or from a group consisting of asparagine and glutamine, and the derivatives thereof; and U ($X_1$, $X_6$, $X_{10}$, $X_{12}$ or $X_{15}$) represents more than one amino acid residue selected from a group consisting of glycine, serine, alanine and threonine, and the derivatives thereof.

As for the peptide of the present invention represented by the above <Chemical Formula 2>, it is preferable to select one from a group consisting of leucine, isoleucine and valine for X, one from a group consisting of asparagine, glutamine, histidine, lysine and arginine for B, one from a group consisting of alanine, serine, and glycine for U, and select cysteine for C (SEQ ID NO: 14).

For building the peptide of the present invention represented by the above <Chemical Formula 2>, it is more preferable to select alanine for $U_4$, leucine for $X_5$, leucine for $X_6$, histidine for $B_7$, histidine for $B_8$, glycine for $U_9$, leucine for $X_{10}$, asparagine for $B'_{11}$, cysteine for $C_{12}$, alanine for $U_{13}$, lysine for $B_{14}$, glycine for $U_{15}$, valine for $X_{16}$, leucine for $X_{17}$ and alanine for $U_{18}$ (SEQ ID NO:15). Thus, it is most preferable for the peptide of the present invention to have amino acid sequence represented by SEQ. ID No 2.

The present invention further provides a peptide in dimer form represented by <Chemical Formula 3> wherein the cysteine residues of two peptides, each represented by <Chemical Formula 1> (SEQ ID NO:11), are combined with each other by disulfide bond.

<Chemical Formula 3>

$$W_1X_2B'_3U_4X_5X_6B_7B_8U_9X_{10}B'_{11}C_{12}U_{13}B_{14}U_{15}X_{16}X_{17}U_{18}$$
$$|$$
$$W_1X_2B'_3U_4X_5X_6B_7B_8U_9X_{10}B'_{11}C_{12}U_{13}B_{14}U_{15}X_{16}X_{17}U_{18}$$

The above amino acids represented by each figures are the same as represented by <Chemical Formula 1> and the peptide is most preferably formed by combining two amino acids of peptides represented by SEQ. ID. No 1, the 12$^{th}$ amino acid each, together by disulfide bond.

The present invention also provides a peptide in dimer form represented by <Chemical Formula 4> wherein the cysteine residues of two peptides, each represented by <Chemical Formula 2> (SEQ ID NO:13), are combined with each other by disulfide bond.

<Chemical Formula 4>

$$U_4X_5X_6B_7B_8U_9X_{10}B'_{11}C_{12}U_{13}B_{14}U_{15}X_{16}X_{17}U_{18}$$
$$|$$
$$U_4X_5X_6B_7B_8U_9X_{10}B'_{11}C_{12}U_{13}B_{14}U_{15}X_{16}X_{17}U_{18}$$

The above amino acids represented by each figures are the same as represented by <Chemical Formula 2> and the peptide is most preferably formed by combining two amino acids of peptides represented by SEQ. ID. No 2, the 9$^{th}$ amino acid each, together by disulfide bond.

The present invention also provides a peptide in dimer form represented by <Chemical Formula 5> wherein the cysteine residue of the peptide represented by <Chemical Formula 1> (SEQ ID NO:11) is combined with that of the peptide represented by <Chemical Formula 2> (SEQ ID NO:13) by disulfide bond.

<Chemical Formula 5>

$$W_1X_2B'_3U_4X_5X_6B_7B_8U_9X_{10}B'_{11}C_{12}U_{13}B_{14}U_{15}X_{16}X_{17}U_{18}$$
$$|$$
$$U_4X_5X_6B_7B_8U_9X_{10}B'_{11}C_{12}U_{13}B_{14}U_{15}X_{16}X_{17}U_{18}$$

The above amino acids represented by each figures are the same as represented in <Chemical Formula 1> and <Chemical Formula 2>. For the peptide above, it is most preferable to combine the 12$^{th}$ amino acid of the peptide represented by SEQ. ID. No 1 and the 9$^{th}$ amino acid of the peptide represented by SEQ. ID. No 2 by disulfide bond.

In the preferred embodiment of the present invention, the present inventors separated a peptide represented as <Chemical Formula 5> from body fluid of *Halocynthia aurantium* and confirmed that the peptide had antimicrobial activity. We, the present inventors named the peptide "halocidin". By detecting out the structure of halocidin, the present inventors confirmed that halocidin consisted of peptides represented as <Chemical Formula 1> and <Chemical Formula 2> in which cysteine residues were combined each other by disulfide bond (see FIG. 5). Named a peptide represented as <Chemical Formula 1>"18Hc" and a peptide represented as <Chemical Formula 2>"15Hc". In order to analyze the characteristics of halocidin, the present inventors prepared peptides in dimer form each represented as <Chemical Formula 3> and <Chemical Formula 4> using peptides represented as <Chemical Formula 1> and <Chemical Formula 2>, and then named them "di-18Hc" and "di-15Hc".

The inventors also named a peptide wherein a C-terminal amino acid was eliminated from 18Hc "(18-1)Hc" and a peptide wherein two C-terminal amino acids were eliminated "(18-2)Hc". In the same manner, Peptides wherein 3 to 6 C-terminal amino acids were removed were named "(18-3) Hc", "(18-4)Hc", "(18-5)Hc" and "(18-6)Hc" respectively. A peptide wherein all histidine residues were substituted with lysine was named "Hck". When lysine was added to N-terminal of a peptide, the letter "K" was added in the first place of the name of the peptide and the added number of lysine was marked as (+) next to the number. For example, as one lysine was added to N-terminal of 18Hc, it was named "K(18+1) Hc".

The mass of peptides represented as <Chemical Formula 1 to 5> was measured, resulting in 1,929 Da, 1,516 Da, 3,861 Da, 3,031 Da and 3,445 Da, respectively (see Table 3). Especially, pI value of halocidin, a peptide represented as <Chemical Formula 5>, was 8.965 and halocidin was a peptide in hetero-dimer form having helical wheel structure (see FIG. 8).

In order to confirm if the peptides of the present invention represented as <Chemical Formula 1 to 5> have antimicrobial activity, performed radical diffusion analysis (see FIG. 9), colony counting analysis (see FIG. 10), hemolysis analysis (see FIG. 11), radical diffusion analysis on Gram negative strain (see FIG. 12, FIG. 13 and FIG. 14) and radical diffusion analysis on Gram positive strain (see FIG. 15, FIG. 16 and FIG. 17). As a result, it was disclosed that those peptides represented as <Chemical Formula 1 to 5> had great antimicrobial activity. Precisely, peptides in dimer forms represented as <Chemical Formula 2, 4 and 5> had greater antimicrobial activity and a peptide represented as <Chemical Formula 2> showed the greatest antimicrobial activity, above all.

In order to confirm if the peptides of the present invention still keep antimicrobial activity under strict conditions in vivo, measured antimicrobial activity of the peptides under the condition of pH 5.5 that was the same acidic condition as the environment in epithelial cells, urethra, vagina, etc, and NaCl 200 mM that was higher than basic condition of intrablood (NaCl 150 mM). As a result, it was confirmed that a peptide represented as <Chemical Formula 5> showed antimicrobial activity under the condition of pH 5.5-pH 7.4 (see Table 4) and NaCl 100 mM-NaCl 200 mM as well (see Table 5).

Based on the above results, the peptides of the present invention represented as <Chemical Formula 1 to 5> were proved to have excellent antimicrobial activity, comparing to the conventional antibiotics. Particularly, the peptides were confirmed to have excellent antimicrobial activity under strong acidic and basic environments, and have strong antimicrobial activity against resistant bacteria.

The present invention further provides an antimicrobial agent containing the above-mentioned peptide as an active ingredient.

As explained hereinbefore, the peptide of the present invention has an excellent antimicrobial activity under strong acidic and basic environments. So, it can be effectively used as an antimicrobial agent.

Thus, the peptide of the present invention can be included as an active ingredient for preparing an antimicrobial agent. The antimicrobial agent of the present invention can be administered orally or parenterally and be used in general form of pharmaceutical formulation.

The antimicrobial agent of the present invention can be prepared for oral or parenterally administration by mixing with generally-used fillers, extenders, binders, wetting agents, disintegrating agents, diluents such as surfactant, or excipients. Solid formulations for oral administration are tablets, pill, dusting powders and capsules. These solid formulations are prepared by mixing one or more suitable excipients such as starch, calcium carbonate, sucrose or lactose, gelatin, etc with one or more halocidin. Except for the simple excipients, lubricants, for example magnesium stearate, talc, etc, can be used. Liquid formulations for oral administrations are suspensions, solutions, emulsions and syrups, and the abovementioned formulations can contain various excipients such as wetting agents, sweeteners, aromatics and preservatives in addition to generally used simple diluents such as water and liquid paraffin. Formulations for parenteral administration are stirilized aqueous solutions, water-insoluble excipients, suspensions, emulsions, and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerinated gelatin, etc.

In general, it has proved advantageous both in human and in veterinary medicine to administer the active compound or compounds according to the present invention in total amounts of about 0.5 mg/kg to about 1 mg/kg, preferably 0.1-0.5 mg/kg of body weight, one to two times every 24 hours, if appropriate, in the form of several individual doses, to achieve the desired results.

The antimicrobial agent of the present invention can be used widely as an antibacterial agent or an antiviral agent to control virus, Gram positive bacteria, Gram negative bacteria, fungi, yeast and protozoa harming plants, animals and human. The antimicrobial agent of the present invention can be used either independently or together with other antibiotics such as erythromycin, tetracycline, azithromycin, vancomycin, cephalosporins, etc. Further, the antimicrobial agent of the present invention can also be used as food additives, cosmetics, ointments, injections, etc.

BRIEF DESCRIPTION OF THE DRAWINGS

The application of the preferred embodiments of the present invention is best understood with reference to the accompanying drawings, wherein.

Lane 1: Acidic extracts of body fluid cells of *Halocynthia aurantium*,

Lane 2: $51^{st}$-$81^{st}$ fractions passed through Sepadex G-50 column,

Lane 3: $35^{th}$-$45^{th}$ fractions passed through Prep. AU-PAGE, and

Lane 4: Halocidin purified by RP-HPLC

Figure 2:
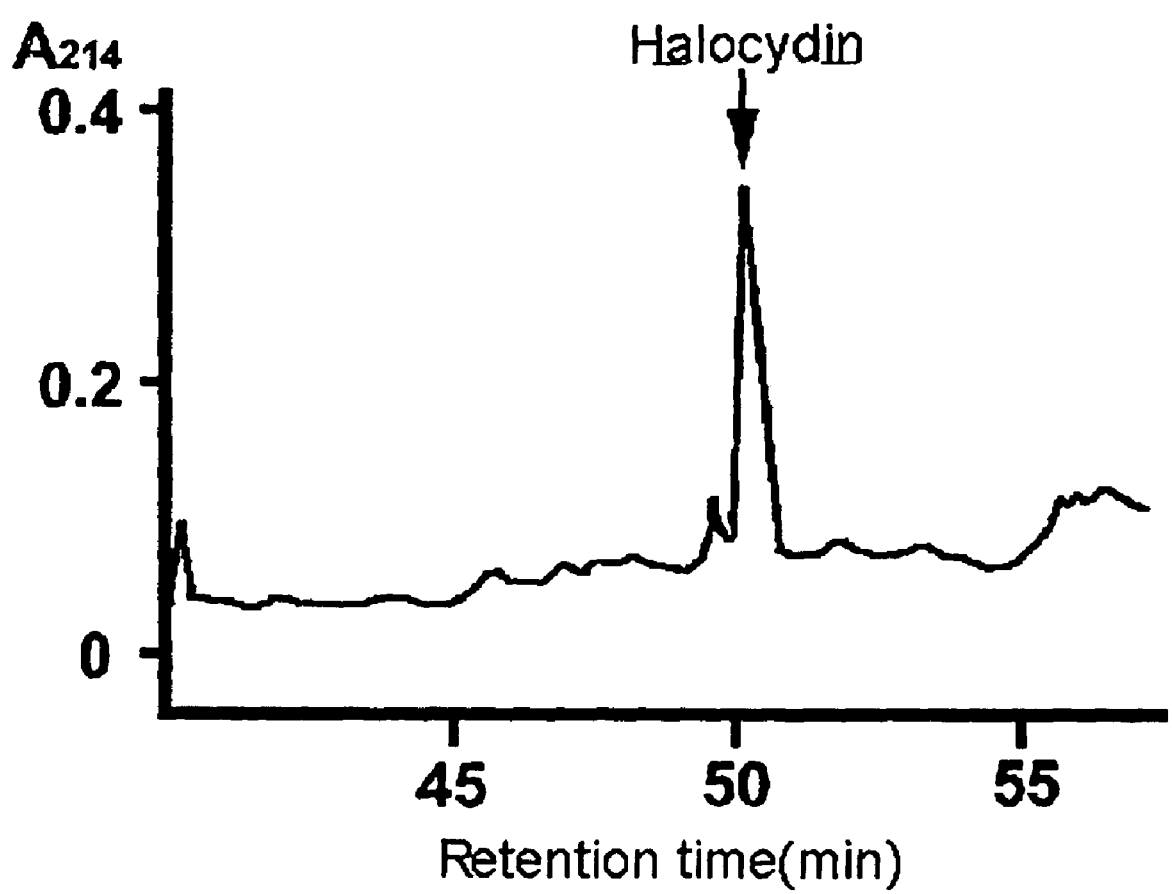
Figure 3:
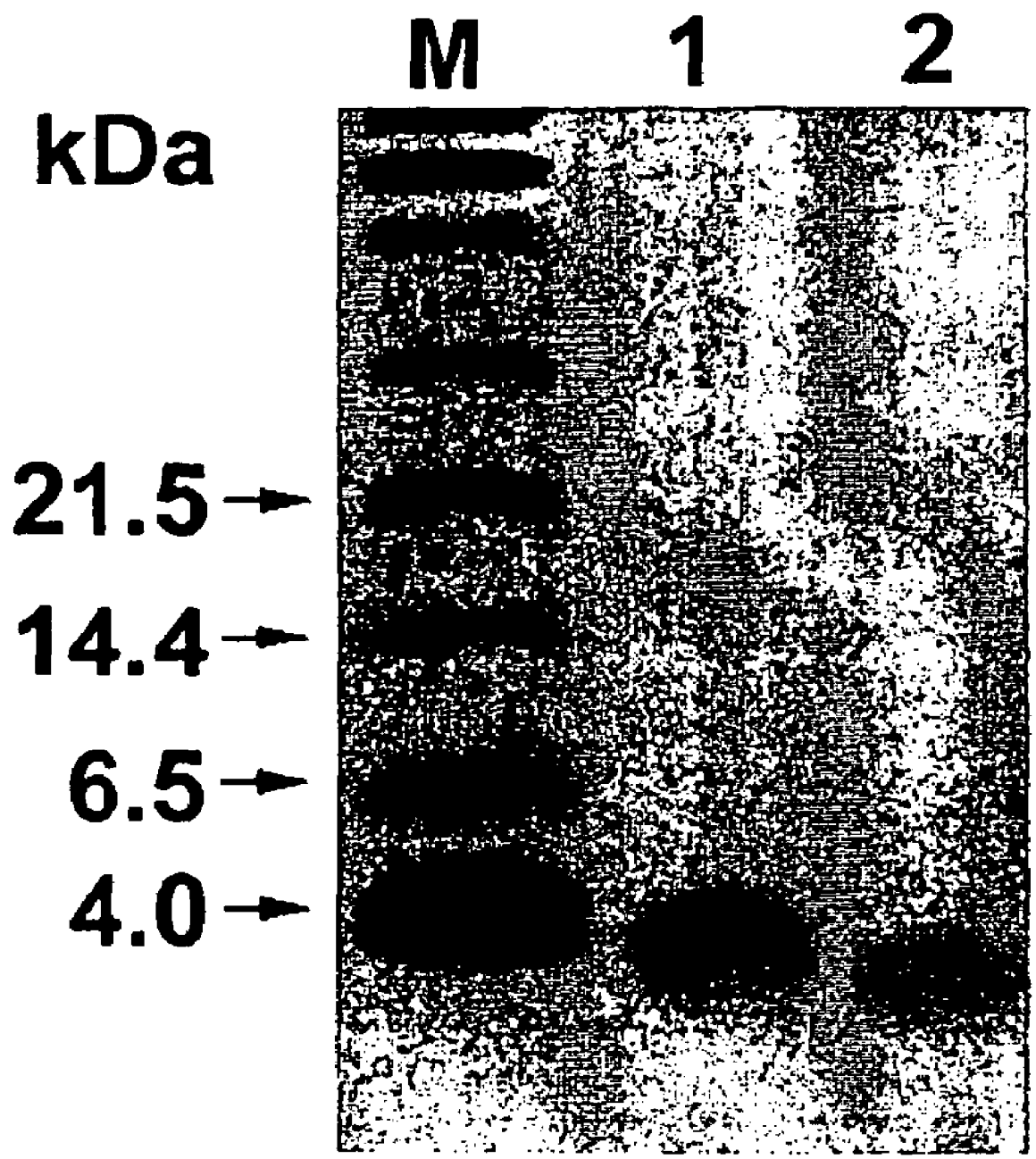

FIG. 2 is a graph showing the result of C18 RP-HPLC with purified halocidin;

FIG. 3 is a photograph showing the result of SDS-PAGE with purified halocidin;

Lane M: Standard molecular weight marker,

Lane 1: Natural halocidin, and

Lane 2: Halocidin cut by dithiothreitol

Figures 4, 5:
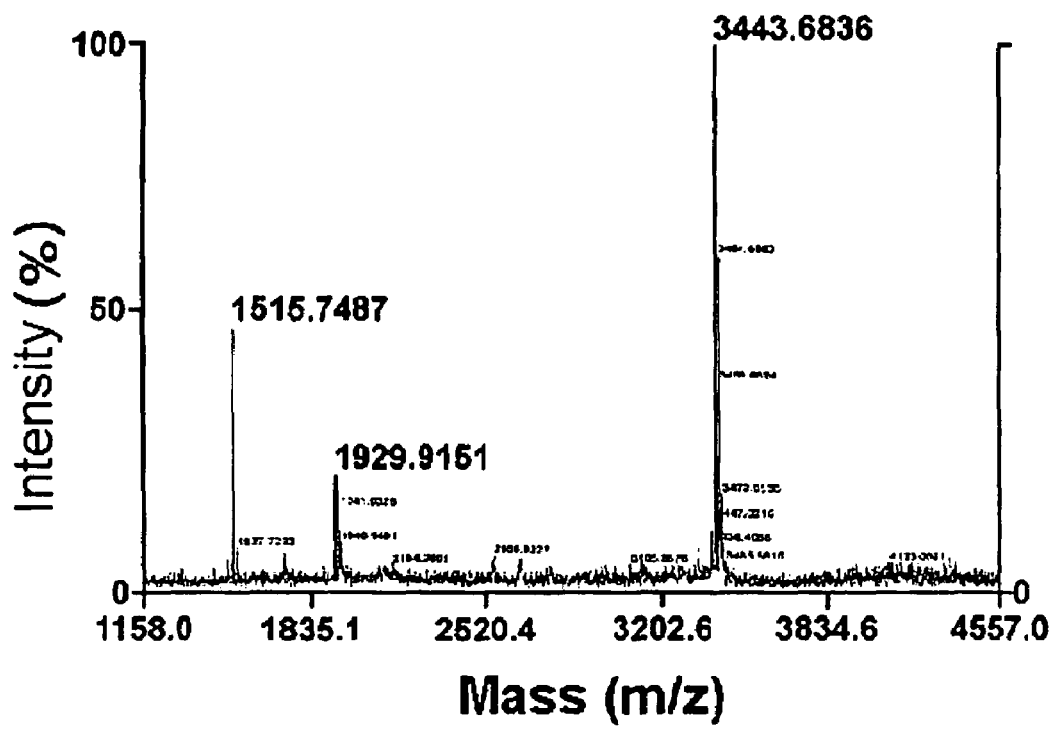

FIG. 4 is a graph showing the result of MALDI mass analysis with purified halocidin;

FIG. 5 is a diagram showing the structure and amino acid sequence of the two constituents of halocidin;

FIG. 6 is a set of graphs showing the result of RP-HPLC with a natural halocidin and a synthetic halocidin;

A: 15Hc and 18Hc,

B: di-15Hc, di-18Hc and halocidin,

C: Natural halocidin

FIG. 7 is a set of graphs showing the CD spectra of 18Hc suspended in phosphate buffer (pH 7.4) (pink line), 20 mM SDS phosphate buffer (pH 7.4) (black line) and 10 mM phosphate buffer containing 50% (v/v) trifluoroethanol (pH 7.4) (red line);

A: 18Hc, B: di-18Hc

Figure 8:
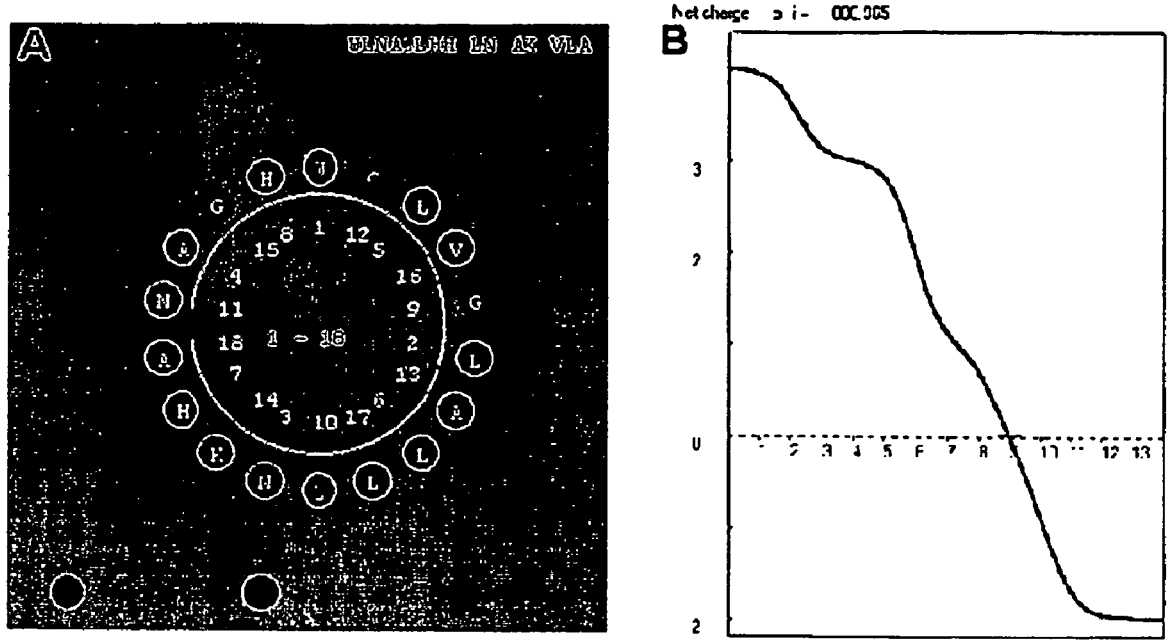
Figure 9:
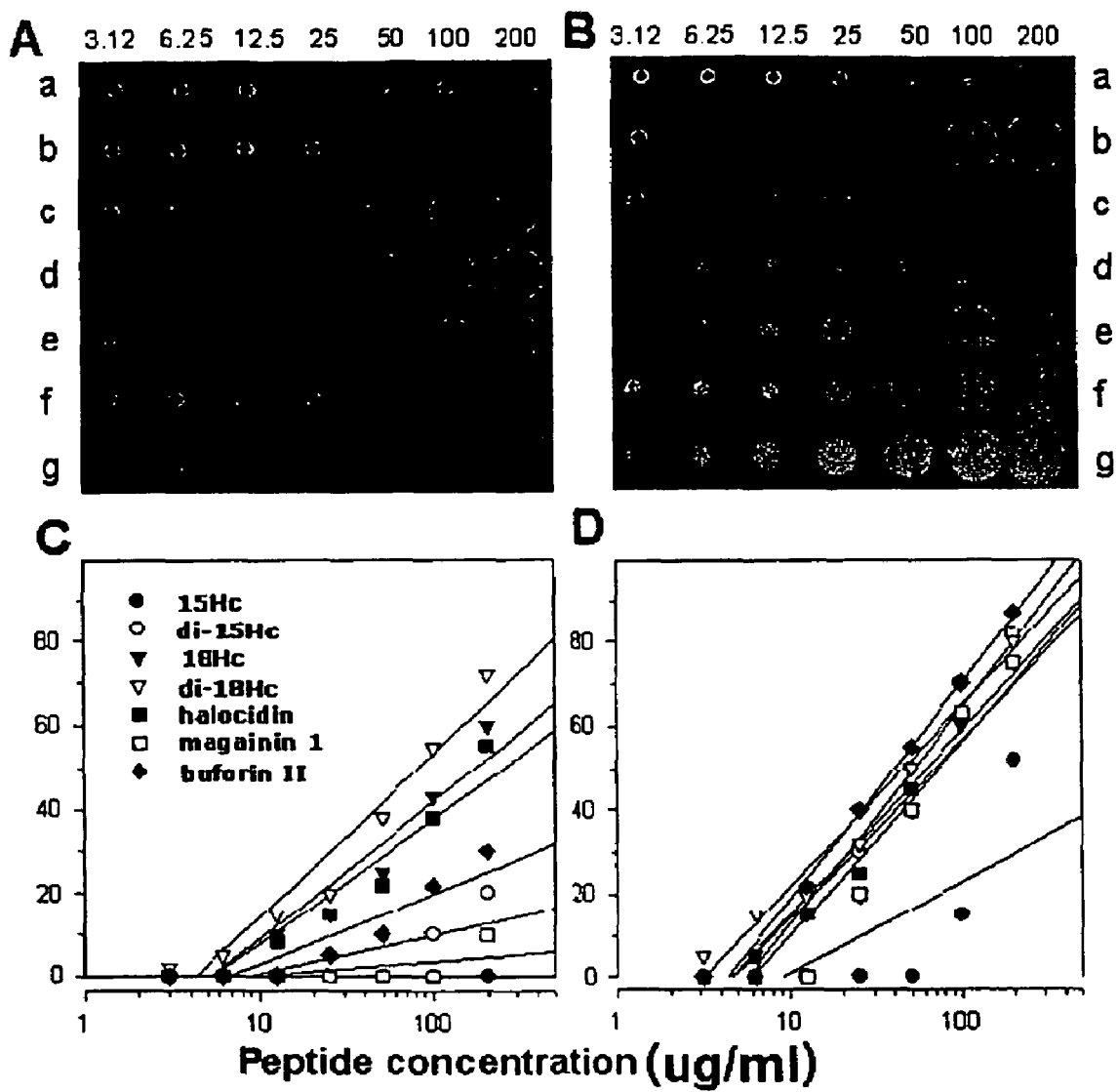

FIG. 8 is a set of a photograph and a graph showing the helical diagram (A) and pI (B) of halocidin (18Hc);

FIG. 9 is a set of photographs and graphs showing the result of radical diffusion analysis of a peptide affecting MRSA (A and C) and MDRPA (B and D);

a: 15Hc,
b: di-15Hc,
c: 18Hc,
d: di-18Hc,
e: Halocidin,
f: Magainin 1,
g: Bufforin 2

Figure 10:
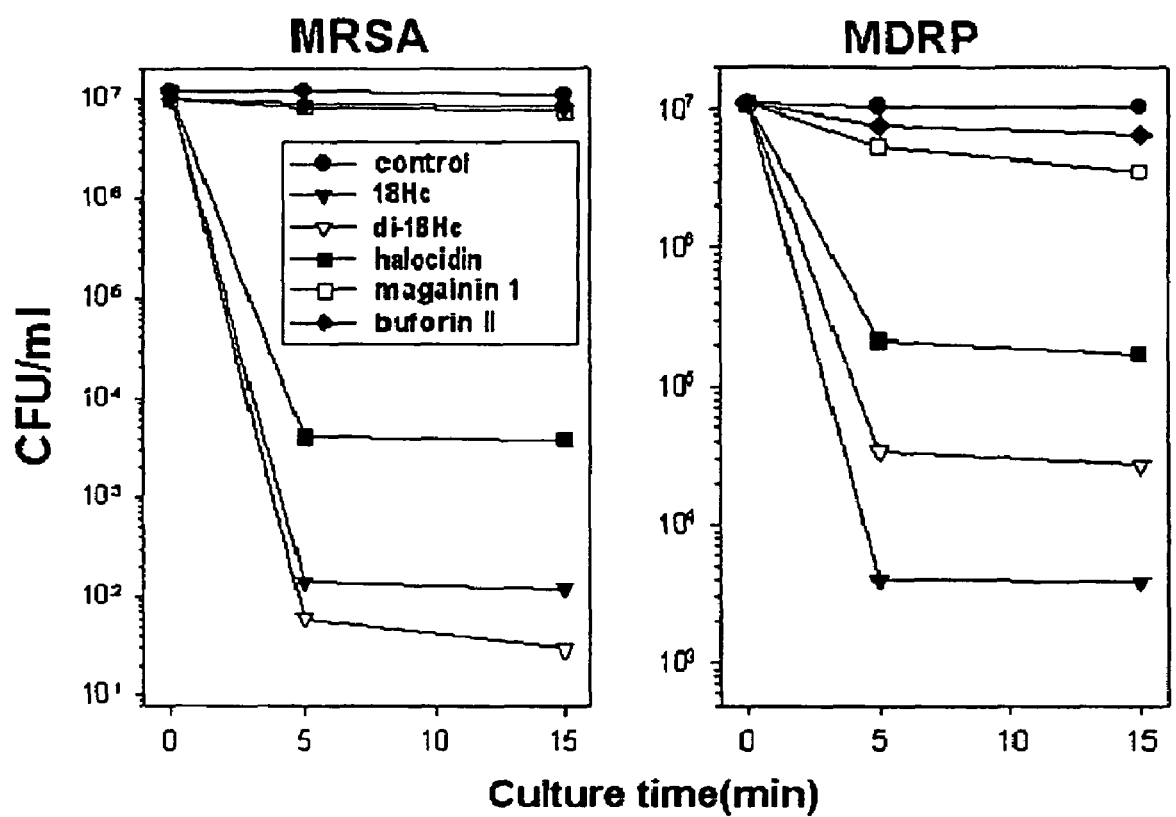
Figure 11:
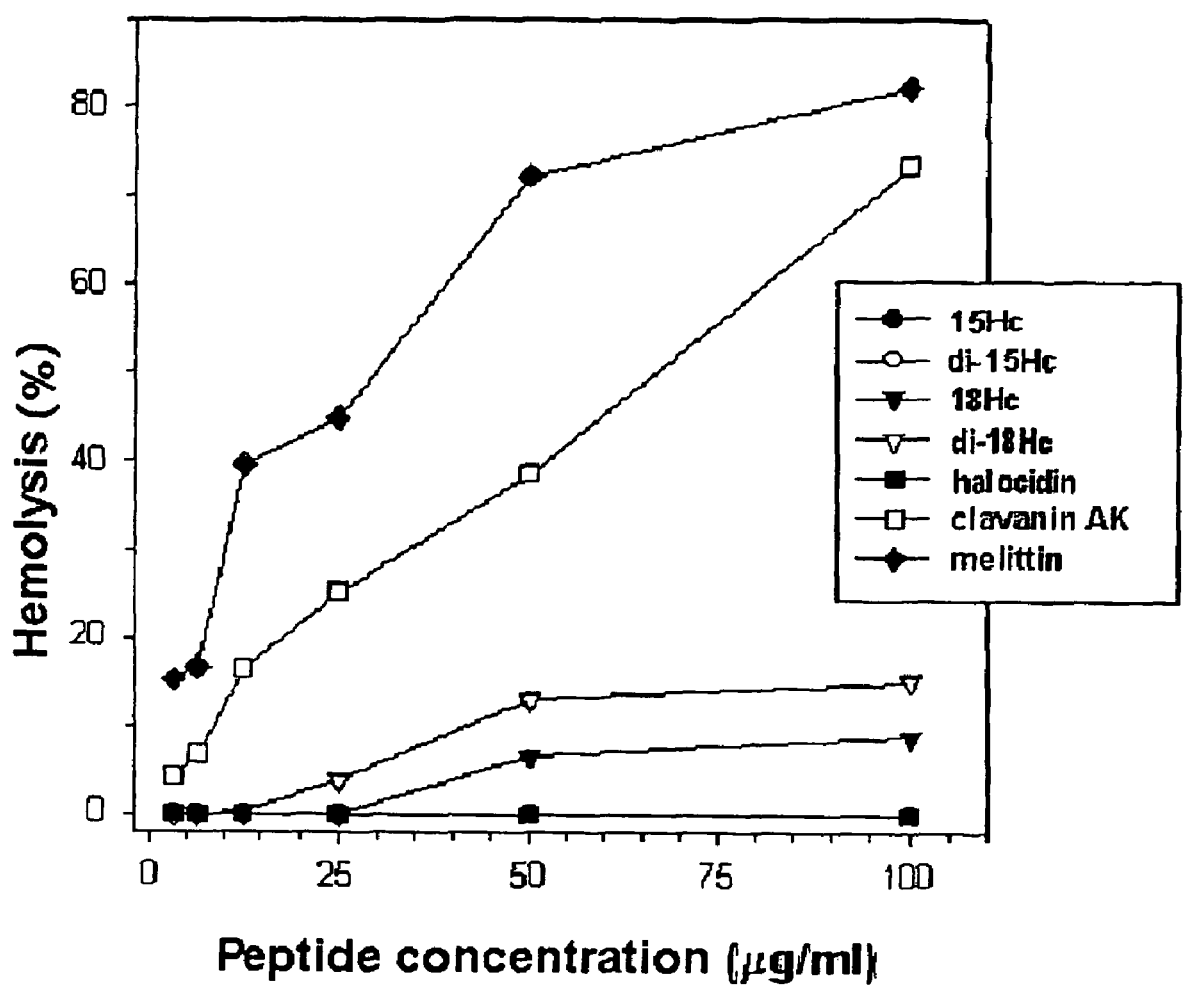
Figure 12:
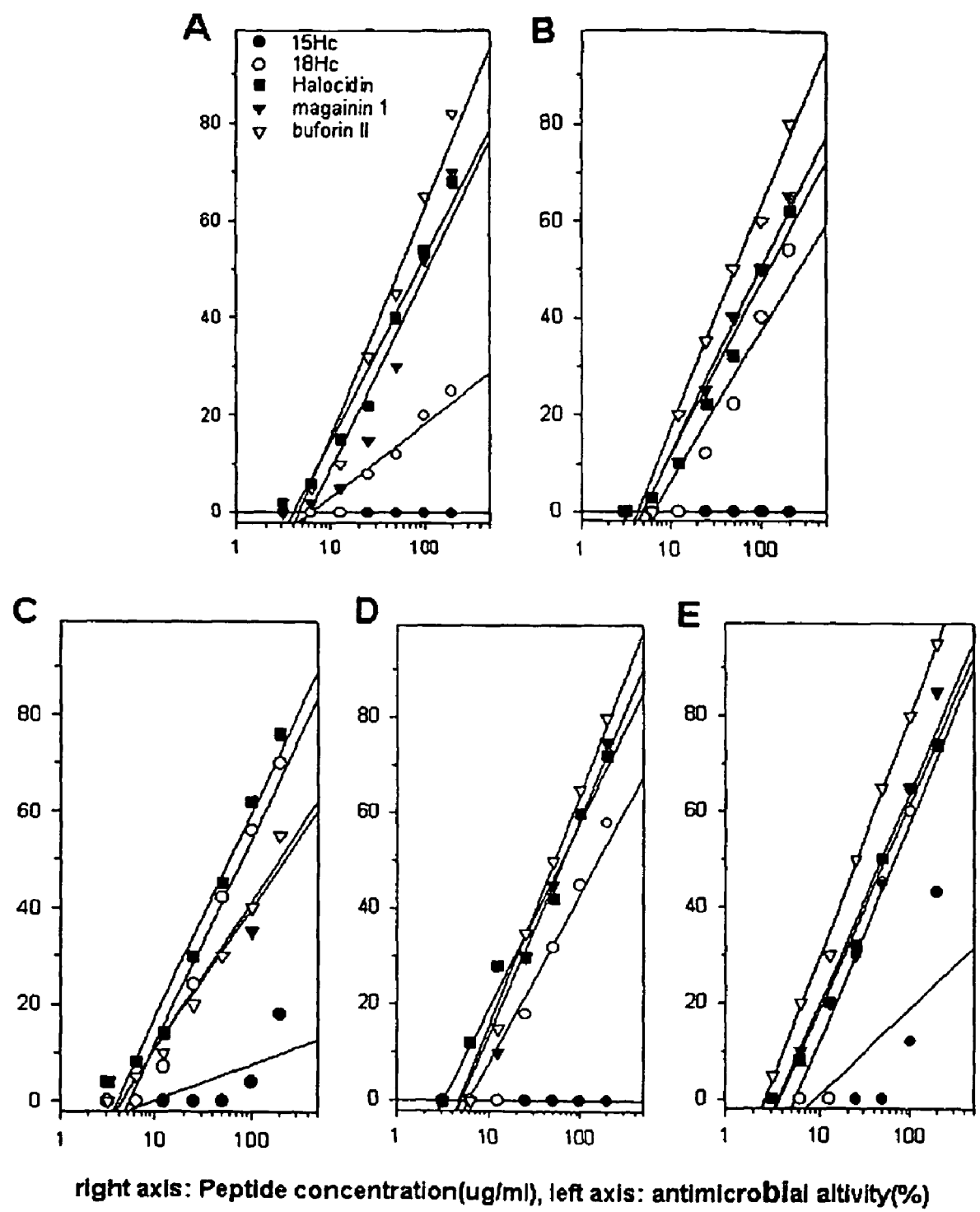

FIG. 10 is a set of graphs showing the antimicrobial activity of a peptide measured by colony counting analysis;

FIG. 11 is a graph showing the result of hemolytic assay with a peptide;

FIG. 12 is a set of graphs comparing antimicrobial activities of 15Hc, 18Hc, halocidin, bufforin 2 and magainin 1 to Gram-negative bacteria;

A: *Pseudomonas aeruginosa*,
B: *Salmonella cholerasuis*,
C: *Salmonella parotyphi* A, D: *E. coli* K112 and
E: *E. coli* DH5α

Figure 13:
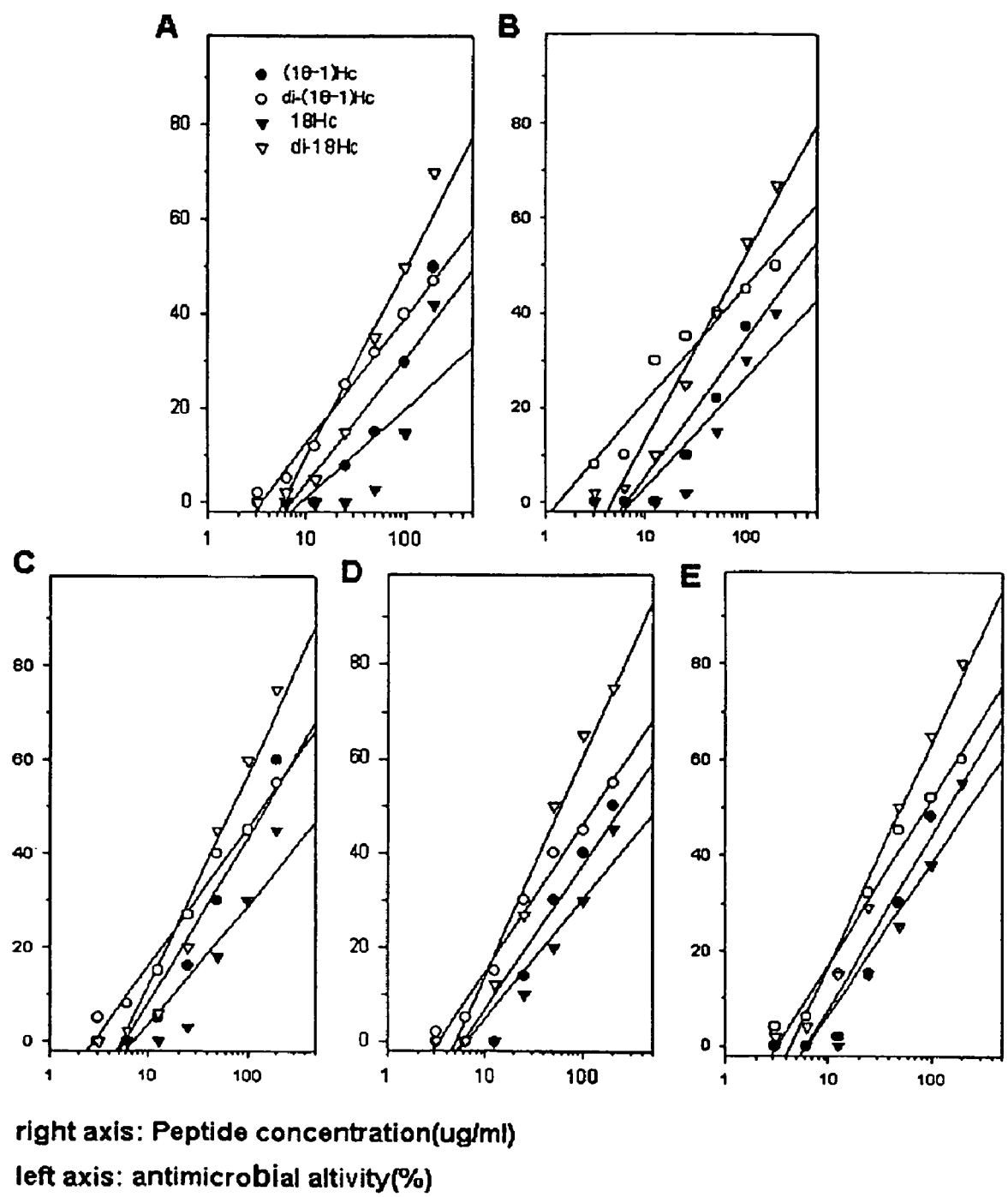

FIG. 13 is a set of graphs comparing antimicrobial activities of (18-1)Hc, di-(18-2)Hc, 18Hc and di-18Hc to Gram-negative bacteria;
A: *Pseudomonas aeruginosa*,
B: *Salmonella cholerasuis*,
C: *Salmonella parotyphi* A,
D: *E. coli* K112 and
E: *E. coli* DH5α

Figure 14:
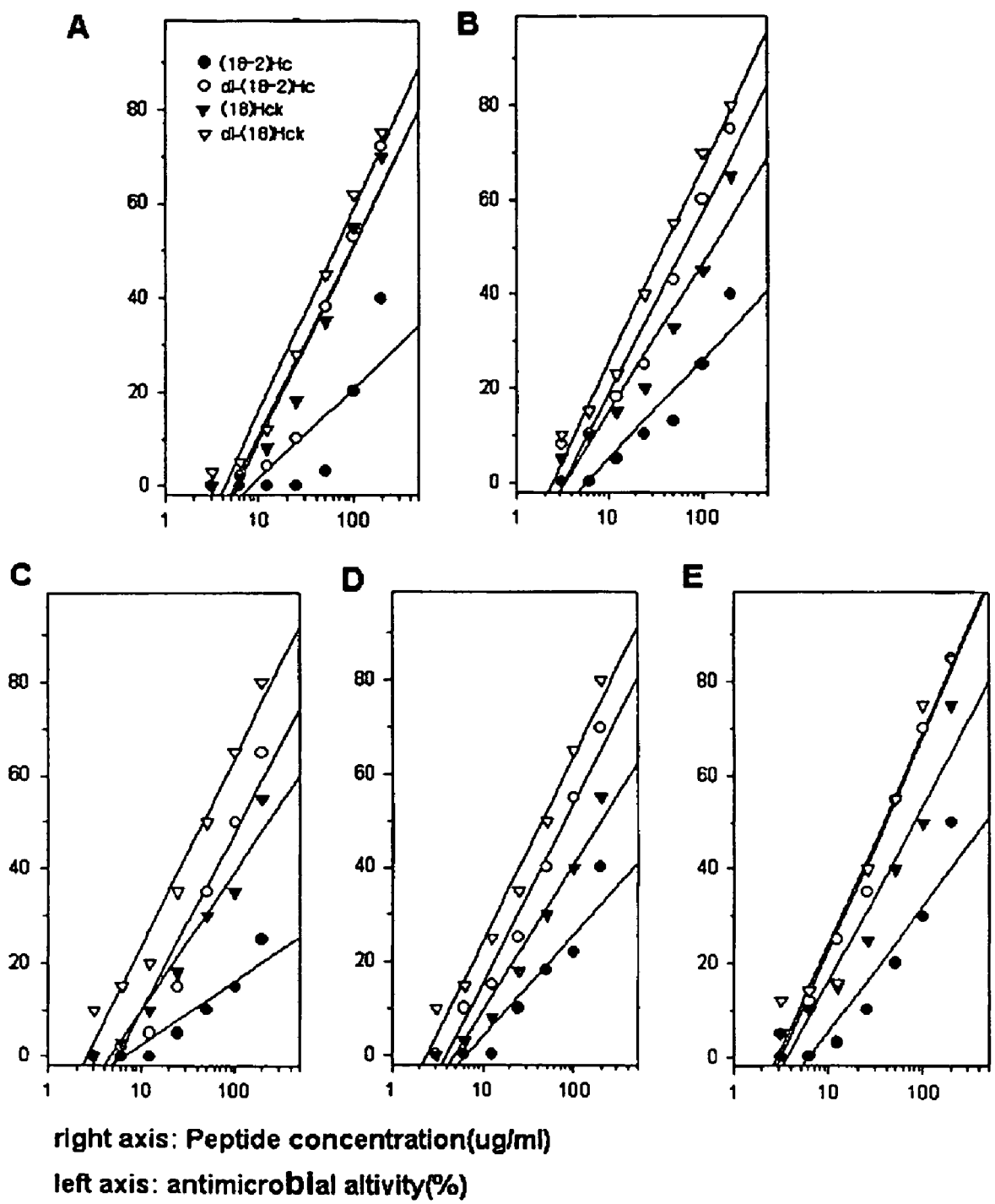

FIG. 14 is a set of graphs comparing antimicrobial activities of (18-2)Hc, di-(18-2)Hc,
(18)Hck and di-(18)Hck to Gram-negative bacteria;
A: *Pseudomonas aeruginosa*,
B: *Salmonella cholerasuis*,
C: *Salmonella parotyphi* A,
D: *E. coli* K112 and
E: *E. coli* DH5α

Figure 15:
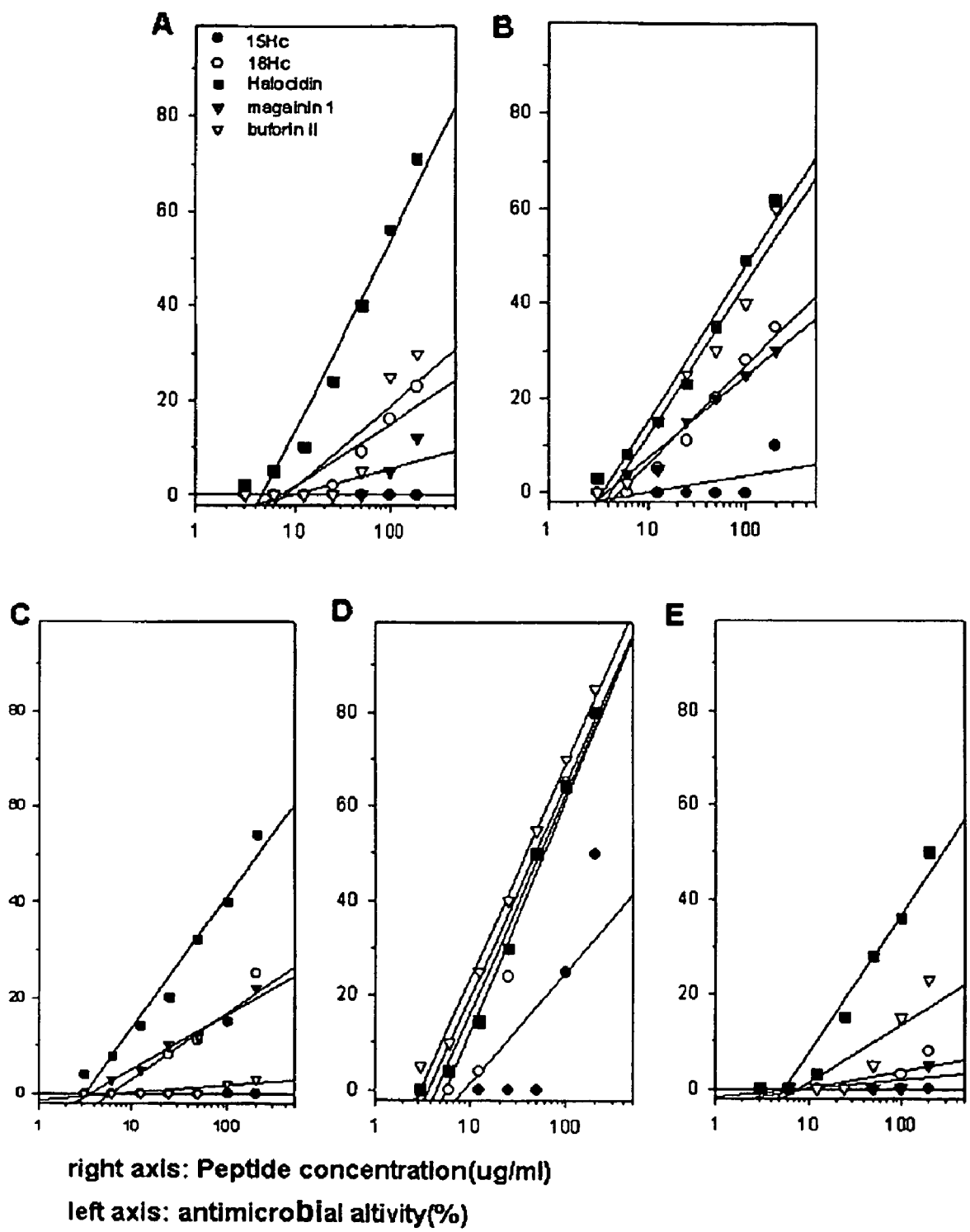
Figure 17:
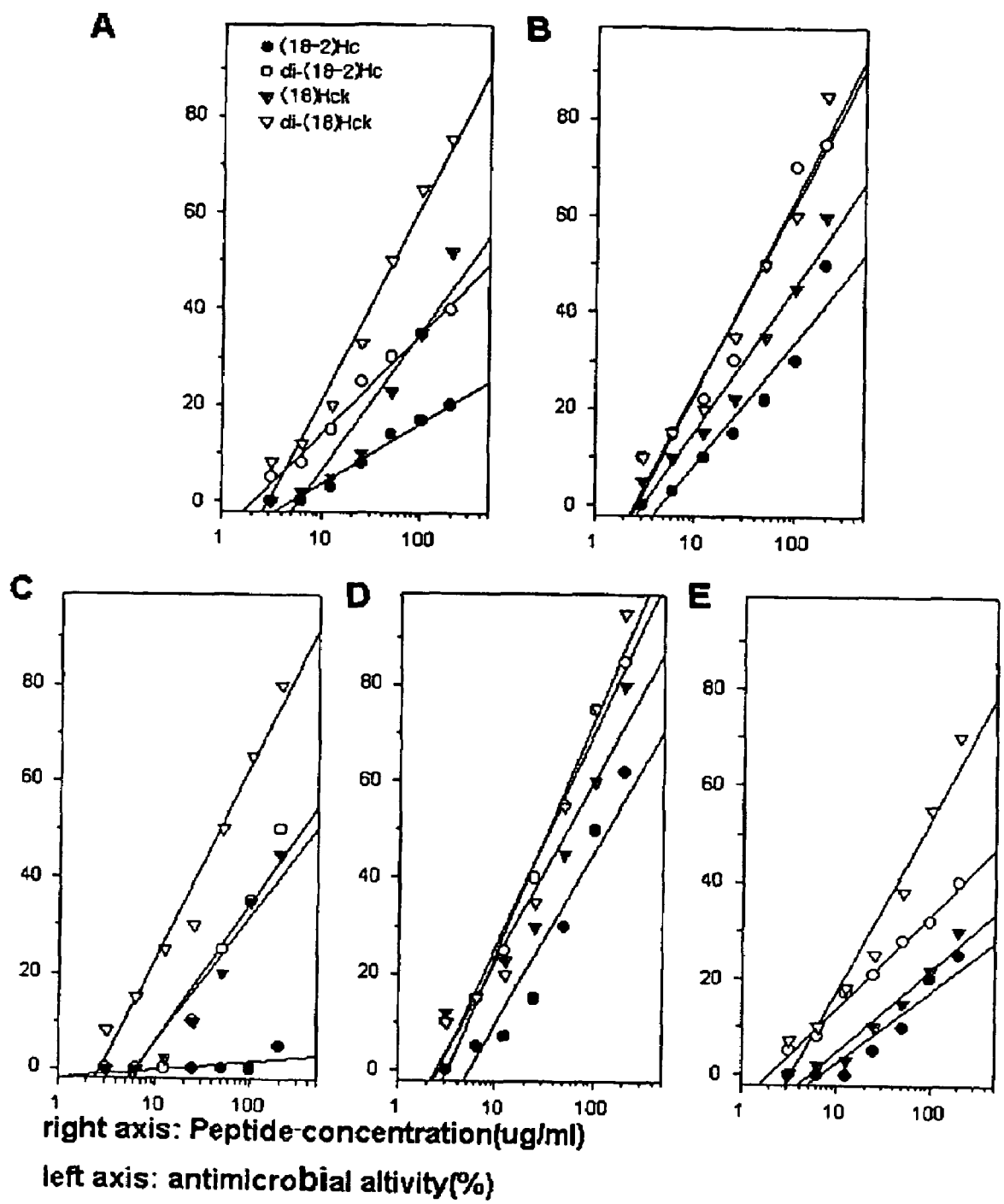

FIG. 15 is a set of graphs comparing antimicrobial activities of 15Hc, 18Hc, halocidin, bufforin 2 and magainin 1 to Gram-positive bacteria;
A: *Staphylococcus aureus*,
B: *Micrococcus luteus*,
C: *Enterococcus faecalis*,
D: *Bacillus subtilus* and
E: MRSA FIG. 16 is a set of graphs comparing antimicrobial activities of (18-1)Hc, di-(18-1)Hc, 18Hc and di-18Hc to Gram-positive bacteria;
A: *Staphylococcus aureus*,
B: *Micrococcus luteus*,
C: *Enterococcus faecalis*,
D: *Bacillus subtilus* and
E: MRSA FIG. 17 is a set of graphs comparing antimicrobial activities of (18-2)Hc, di-(18-2)Hc,
(18)Hck and di-(18)Hck to Gram-positive bacteria;
A: *Staphylococcus aureus*,
B: *Micrococcus luteus*,
C: *Enterococcus faecalis*,
D: *Bacillus subtilus* and
E: MRSA

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Isolation of an Antimicrobial Peptide from *Halocynthia aurantium*

<1-1> Isolation of Acid Extract from *Halocynthia aurantium*

Bought *Halocynthia aurantium*, called silky sea squirt, at a fish market in Sockcho, Kangwon-Do, Korea, washed the outer skin alive with 70% ethanol, and dried thereof. Cut the exhalent opening of the dried tunicates crossways and put thereof into a 50 ml tube containing 150 mg of EDTA to collect hemolymph. Removed impurities from the obtained hemolymph using 74 μm pore sized mesh filter (Netwell, Corning Costar, Cambridge, Mass., USA), after which centrifuged thereof at 4° C. with 300 g for 30 minutes. After centrifugation, suspended precipitated body fluid cells, hemocytes, in 30 ml of 0.34 M sucrose solution and centrifuged again at 4° C. with 300 g for 30 minutes. On completing centrifugation, isolated newly formed cell layer and suspended thereof in 10 ml of cooled 5% acetic acid solution. After sonication with the above suspension 5 times 15 seconds each, added 40 ml of 5% acetic acid solution thereto. Mixed the solution extracted by acetic acid at 4° C. for overnight, followed by centrifuging at 4° C. with 20,000 g for 30 minutes. Used the obtained supernatants from centrifugation as a test material for purifying antimicrobial peptides.

Quantified the protein of acid extracts from *Halocynthia aurantium* using bicinchoninic acid (Sigma) and obtained eluting fractions by loading the supernatants containing at least 50 mg of protein to Sephadex G-50 gel filtering column (Sigma) equilibrated with 5% acetic acid solution.

<1-2> Antimicrobial Activity of Acid Extracts of *Halocynthia aurantium*

In order to measure the antimicrobial activity of acid extracts of *Halocynthia aurantium* obtained in the above Example <1-1>, the present inventors performed ultrasensitive radial diffusion assay. Particularly, analyzed 150 fractions eluted in the above Example <1-1> 5 times each. Took 100 μl from 2 ml of each fraction and concentrated thereof with a vacuum centrifugation (Centra Evaporator, Bioneer, Korea), which was suspended in 5 μl of 0.01% acetic acid solution. Meanwhile, prepared agarose plate including wells 3 mm in diameter by adding methicillin resistance *Staphylococcus aureus* (referred as "MRSA" hereinafter, Seoul Women's University, Korea CCARM3001) of mid-logarithmic phase to gel comprising sterilized citrate phosphate buffer (9 mM sodium phosphate, 1 mM sodium citrate, pH 7.4), 1% (w/v) type 1 agarose (low electroendosmosis agarose) (A 6013, Sigma) and 3% tryptic soy broth (TSB, Difco, Detroit, Mich., USA). Loaded the above fractions onto the wells of agarose plate containing the above bacteria. Reacted thereof for 3 hours to make the peptides spread into the agarose gel. Added 10 ml of overnutrition medium comprising 6% TSB and 1% agarose gel thereto. Cultured the above plate for overnight until the colonies of the above bacteria were formed. Confirmed the antimicrobial activity of the loaded peptide by measuring the diameter of clearing zone formed around the loaded peptide fraction.

As a result, the clearing zones formed around #51-#81 peptide fractions were the biggest, suggesting that the fractions had high antimicrobial activity.

<1-3> Purification of Peptide in Fractions Having Antimicrobial Activity

In order to purify peptide fractions having antimicrobial activity more clearly, centrifuged #51-#81 fractions that were confirmed to have antimicrobial activity in the pre-stage, concentrated and loaded thereof on preparative acid urea polyacrylamide gel electrophoresis (referred "Prep AU-PAGE" hereinafter). Adjusted the current speed of Prep AU-PAGE to 60 ml/hour and divided by 2 ml for a fraction.

Put Prep AU-PAGE fractions in 2 ml tubes and concentrated with a rotary concentrator. Performed electrophoresis with each fraction at intervals of 10 numbers in two AU-PAGE gels. Stained one gel with Coomasie blue to confirm bands and investigated the antimicrobial activity of protein bands of the other gel with gel overlay assay using MRSA. For the gel overlay assay, put the electrophoresed gel on 10 ml of underlay agar containing MRSA and let it to be reacted at 37° C. for 3 hours in order for the peptides to diffuse into agarose gel, after which poured 10 ml of over-nutrition medium (6% TSB and 1% agarose gel).

Figure 1:
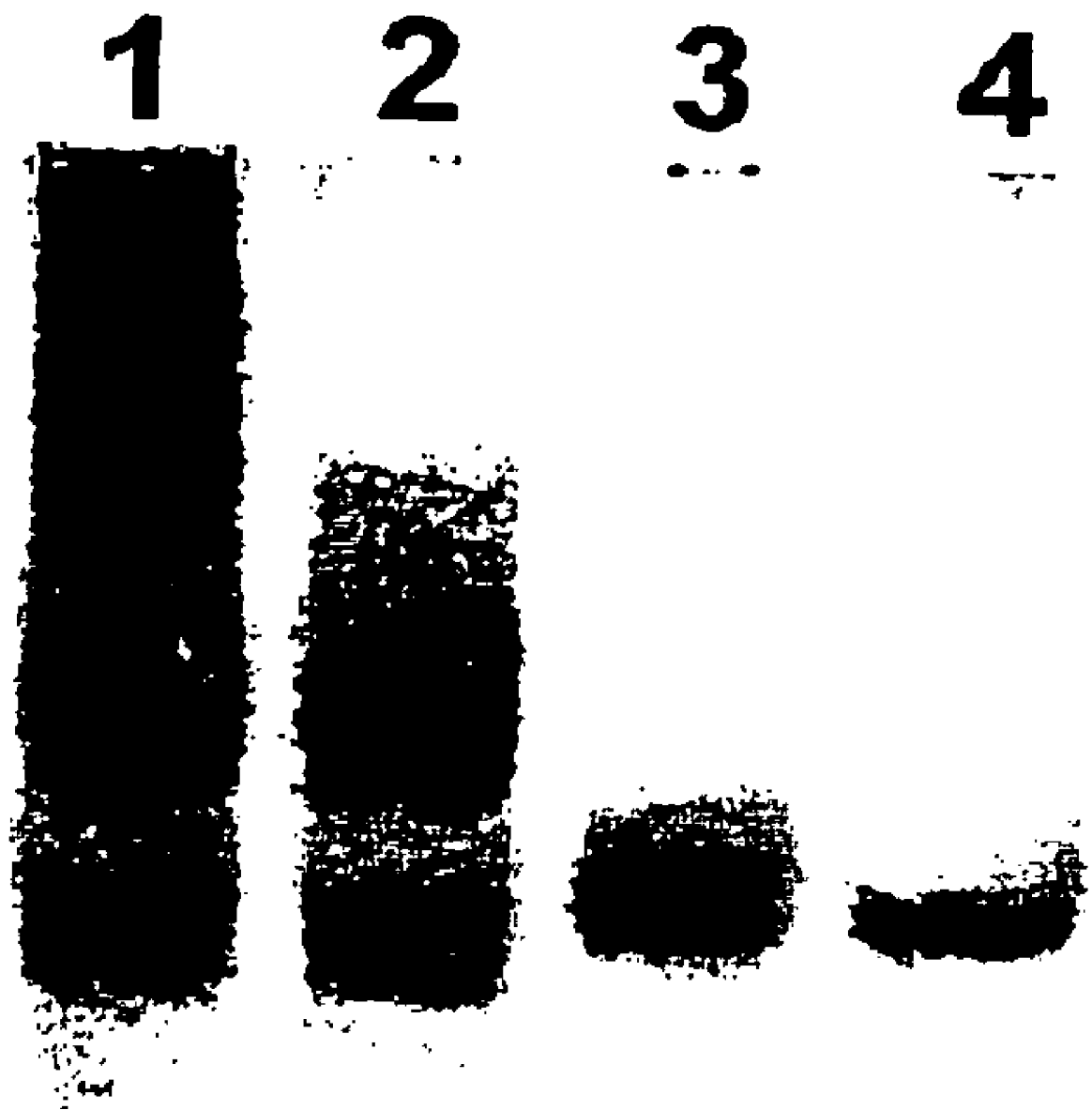
FIG. 1 is an AU-PAGE photograph showing the purification process of halocidin from *Halocynthia aurantium*.

As a result, proteins contained in #35-#45 fractions were confirmed to have antimicrobial activity (FIG. 1).

In order to purify #35-#45 fractions that were confirmed to have antimicrobial activity finally, loaded them to C18 reverse phase high performance liquid chromatography (referred as "RP-HPLC" hereinafter) column (Vydac 218TP54: The Separation Group, Hesperia, Calif.). For the first 10 minutes after loading those samples, washed the column by spilling 5% acetonitrile containing 0.1% trifluoroacetic acid (TFA) at the speed of 0.5 ml/minute. Thereafter, increased the concentration of acetonitrile by 1%/minute for 60 minutes. During the process, collected peak fraction of each concentration of acetonitrile. Concentrated 10% of each collected fraction with a vacuum rotary concentrator, followed by confirming antimicrobial activity with radial diffusion analysis.

As a result, confirmed that a peptide isolated at 50.2 minute at which the concentration of acetonitrile reached 45.2% had antimicrobial activity and named it "halocidin" (FIG. 2).

Example 2

Analysis of Characteristics of Purified Halocidin

<2-1 Mass Analysis of Halocidin

In order to clarify characteristics of halocidin, a novel peptide having antimicrobial activity, isolated from *Halocynthia aurantium* in the above Example 1, the present inventors performed SDS-PAGE (sodium dodecyl sulfate-polyacrylamide gel electrophoresis) and AU-PAGE. Particularly, after freeze-drying halocidin, a peptide having antimicrobial activity, isolated in the above Example 1, added 25 μl of 8 M urea and 25 μl of 0.4 M ammonium bicarbonate (pH 8.0) and melted. Added 45 mM dithiothreitol thereto and induced reaction at 50° C. for 15 minutes. In order to produce a vinylpyridine derivative of halocidin monomer, added 15 μl of vinylpyridine to the above halocidin mixture and cooled thereof at room temperature, after which let the mixture to be reacted in the dark condition at least for 30 minutes. Extracted the final reactants with RP-HPLC. Performed Tricine SDS-PAGE and AU-PAGE to confirm whether the product was correctly extracted, measured the molecular weight of the extracted halocidin with MALDI (matrix-associated laser desorption ionization) mass analyzer (Voyager-DE STR, Per-Septive Biosystems, USA) and analyzed amino acid sequences with a Gas-phase Edman degradation method using Procise 419 (Applied Biosystems, USA).

As a result, it was confirmed that the mass of halocidin extracted by RP-HPLC and halocidin monomers cut by dithiotreitol were 3.4 kDa and 1.5 and 1.8 kDa respectively (FIG. 3), and major peak of halocidin was seen at the point of 3443.6836 m/z and minor peaks were seen at the points of 1515.7487 m/z and 1929.9151 m/z (FIG. 4). The structure of halocidin was also confirmed in which cysteine residues of a monomer consisting of 18 amino acids was combined with cysteine residues of another monomer consisting of 15 amino acids by disulfide bond (FIG. 5).

Conclusively, the present inventors found out that halocidin, a peptide having antimicrobial activity isolated from *Halocynthia aurantium*, has 3,443.7 Da molecular weight and is constructed by 15 monomer and 18 monomer in which cysteine residues were combined each other by disulfide bonds. Finally, the present inventors named 18 monomer and 15 monomer forming halocidin "18Hc" and "15Hc" respectively.

<2-2> Preparation of Synthetic Halocidin and Comparing the Mass of the Synthetic Halocidin with that of *Halocynthia aurantium* Halocidin After confirming the structure of halocidin formed by 15Hc and 18Hc, the present inventors prepared synthetic peptides in order to analyze and compare the characteristics thereof. Particularly, artificially synthesized halocidin monomers using an automatic solid-phase peptide synthesizer (Pioneer, Applied Biosystems, USA) and purified with RP-HPLC. Mixed 1 mg/ml of each synthesized peptide for homodimer or heterodimer (halocidin) formed by 15 monomer and 18 monomer in 0.1 M ammonium bicarbonate solution and let the mixture in the air over 72 hours, resulted in the completion of synthetic peptides. Measured the mass of synthesized monomers, homodimers and heterodimers using a MALDI mass analyzer, by which confirmed if halocidin was correctly synthesized.

The sequences of synthesized peptide monomers are shown in Table 2.

TABLE 2

| Peptide | Sequence | Sequence list |
|---|---|---|
| 18Hc | WLNALLHHGLNCAKGVLA | SEQ. ID. No 1 |
| (18-1)Hc | WLNALLHHGLNCAKGVL | SEQ. ID. No 3 |
| (18-2)Hc | WLNALLHHGLNCAKGV | SEQ. ID. No 4 |
| (18-3)Hc | WLNALLHHGLNCAKG | SEQ. ID. No 2 |
| (18-4)Hc | WLNALLHHGLNCAK | SEQ. ID. No 5 |
| (18-5)Hc | WLNALLHHGLNCA | SEQ. ID. No 6 |
| (18-6)Hc | WLNALLHNGLNC | SEQ. ID. No 7 |
| (18)Hck | WLNALLKKGLNCAKGVLA | SEQ. ID. No 8 |
| K(18 + 1)Hc | KWLNALLHHGLNCAKGVLA | SEQ. ID. No 9 |
| K(18 + 1)Hck | KWLNALLKKGLNCAKGVLA | SEQ. ID. No 10 |

As a result, it was confirmed that the expected masses of *Halocynthia aurantium* halocidin and synthetic halocidin and the masses after measuring with a MALDI mass analyzer were all the same (Table 3).

TABLE 3

| Peptide | | Expected mass | MALDI measured mass |
|---|---|---|---|
| *Halocynthia aurantium* halocidin | 15Hc | 1515.9 | 1515.74 |
|  | 18Hc | 1929.4 | 1929.91 |
|  | Halocidin | 3443.3 | 3443.68 |
| Synthetic halocidin | 15Hc | 1515.9 | 1515.70 |
|  | 18Hc | 1929.4 | 1928.92 |
|  | di-15Hc | 3029.8 | 3031.07 |
|  | di-18Hc | 3856.8 | 3861.06 |
|  | Halocidin | 3443.3 | 3445.04 |

<2-3> Comparison of Elution Peaks of *Halocynthia aurantium* Halocidin and Synthetic Halocidin The present inventors performed RP-HPLC to reconfirm eluting peaks of *Halocynthia aurantium* halocidin and synthetic halocidin that had same masses as seen in the above Example <2-2>. Particularly, loaded the solution containing *Halocynthia aurantium* halocidin extracted by acetonitrile to RP-HPLC column and spilled 5% acetonitrile into the column for 10 minutes (1 minute/ml). Measured the fractions eluted by the time. As a result, two monomers (15Hc and 18Hc) of *Halocynthia aurantium* were eluted at the 42$^{nd}$ minute with 36.8% acetonitrile concentration and at the 52$^{nd}$ minute with 46.3% acetonitrile concentration respectively (FIG. 6A). Meanwhile, two homodimers, di-15Hc and di-18Hc, were eluted from the fractions with 39.2% acetonitrile concentration and with 51.7% acetonitrile concentration respectively. Heterodimers forming the structure of halocidin were eluted from the fractions with the same acetonitrile concentrations (FIG. 6C) as the case of eluting natural halocidin (FIG. 6B).

<2-4> Identification of the Secondary Structure of Halocidin

In order to identify the secondary structure of halocidin, the present inventors investigated CD spectra of the halocidin. Particularly, suspended 18Hc and di-18Hc in phosphate buffer (pH 7.4), 20 mM SDS phosphate buffer (pH 7.4) and 50% (v/v) trifluorethanol 10 mM phosphate buffer (pH 7.4) at 25° C. using 1 mm rectangular cell. Measured circular dichroism spectrum using CJ-715 CD/ORD sepectropolaimeter (JASCO. Co).

As a result, 18Hc and di-18Hc were confirmed to have α-helix structure having maximum value at the point of 193 nm and two minimum values at the points of 208 nm and 222 nm when being suspended in 20 mM SDS phosphate buffer and 50% (v/v) trifluorethanol 10 mM phosphate buffer (FIG. 7).

<2-5> Measurement of Helical Wheel Diagram and pI

In order to confirm the characteristics of halocidin more accurately, the present inventors measured helical wheel diagram and pI using ANTHEPROT 2000 V 5.2 software. As a result, confirmed the fact that 18Hc has a helical wheel structure and amphipathicity resulted from clustering of polar and non-polar residues (FIG. 8A). Measured electric charges of 18Hc by pH change, resulting in the confirmation that pI of 18Hc is 8.965 (FIG. 8B).

Example 3

Analysis of Antimicrobial Activity of Halocidin

In order to analyze antimicrobial activity of a novel antimicrobial peptide halocidin isolated from *Halocynthia aurantium*, the present inventors performed ultra-sensitive radical diffusion assay, colony counting assay, hemolytic assay and antimicrobial activity analysis against Gram-positive or Gram-negative bacteria.

<3-1> Ultra-Sensitive Radical Diffusion Assay

The present inventors performed ultra-sensitive radical diffusion assay with synthetic peptides prepared in the above Example <2-2>. Particularly, measured antimicrobial activity of each 15Hc, di-15Hc, 18Hc, di-18Hc, halocidin, magainin 1 (Sigma) (control group) and buforin 2 (Sigma) (comparative group) against MRSA and multi drug resistance *Pseudomonas aeruginosa* (referred as "MDRPA" hereinafter)(Seoul Women's University CCARM2002) according to the concentration of the peptides.

As a result, it was confirmed that buforin 2 that was known to have high antimicrobial activity to MRSA strain was proved to have antimicrobial activity by that the diameter of clear zone was enlarged as the concentration increased. 18Hc, di-18Hc and halocidin were confirmed to have higher antimicrobial activity than buforin 2 as the concentration increased. Especially, di-18Hc showed the highest antimicrobial activity (FIG. 9A and FIG. 9C). Meanwhile, magainin 1 and buforin 2 were proved to have antimicrobial activity to MDRPA strain. And, 15Hc, di-15Hc, 18Hc, di-18Hc and halocidin were proved to have higher antimicrobial activity than comparative group (FIG. 9B and FIG. 9D).

Based on the above results, the present inventors confirmed that *Halocynthia aurantium* halocidin has high antimicrobial activity, and especially, peptides in the form of homodimer constructed by 15-monomer and 18-monomer, which are constituents of halocidin, have higher antimicrobial activity rather than halocidin itself.

<3-2> Colony Counting Assay

In order to investigate antimicrobial activity of halocidin, the present inventors performed colony counting assay. Particularly, adjusted the final concentration of the peptide to 5 μg/ml by mixing the peptide and MRSA strain or MDRPA strain of mid-log phase in sterilized 10 mM sodium phosphate buffer (pH 7.4) containing 0.3 mg/id of TSB powder. Adjusted the final volume of the above mixture to 100 μl, and then let it be pre-reacted in a 37° C. shaking water bath for 5 and 15 minutes each. Collected 20 μl of pre-reacted solution and loaded thereof onto 1.5% bacto-agar plate (Difco). Induced reaction for overnight and counted the number of formed colonies on the above plate, from which measured the antimicrobial activity. Used magainin 1 and buforin 2 for comparative group, and 0.01% acetic acid for control group.

As a result, comparative group and control group hardly showed antimicrobial activity to MRSA strain and MDRPA strain while 18Hc, di-18Hc and halocidin showed high antimicrobial activity from 5 minutes after reaction began, which was continued until the 15 minutes after reaction. Especially, di-18Hc showed the highest antimicrobial activity and 18Hc and halocidin followed in order (FIG. 10). From the above results, the present inventors confirmed that 18Hc monomer or dimer, constituents of halocidin, has higher antimicrobial activity than halocidin itself.

<3-3> Hemolytic Assay

In order to investigate antimicrobial activity of halocidin, the present inventors performed hemolytic assay. Particularly, mixed 20 μl of peptide diluted to 100, 50, 25, 12.5, 6.25, 3.125 μg/ml and 180 μl of 2.5% (V/V) human erythrocytes in PBS. Used melittin (Sigma) and clavanin AK, a congener in which clavanin A residue was substituted, for comparative group, and 0.01% acetic acid for control group. After reacting the mixture at 37° C. for 30 minutes, added 600 μl of PBS into each tube. Centrifuged the solution at 10,000 g for 3 minutes and separated supernatants. Measured OD at 540 nm and calculated the hemolytic activity (%) according to the below <Mathematical Formula 1>.

$$\text{Hemolytic Activity}(\%) = \frac{\text{Sample } A_{540} - \text{Control Group } A_{540}}{100\% \text{ Comparative Group } A_{540} - \text{Control Group } A_{540}} \times 100$$

<Mathematical Formula 1>

As a result, the hemolytic activity of each peptide di-18Hc, 18Hc, 15Hc, di-15Hc and halocidin was proved to be 18%, 9%, 0% and 0% (FIG. 11). Therefore the hemolytic activity of di-18Hc was the highest.

<3-4> Comparing Antimicrobial Activity to Gram Negative Bacteria

The present inventors confirmed the antimicrobial activity of halocidin to Gram-negative bacteria with radical diffusion assay. Particularly, investigated antimicrobial activities of 15Hc, 18Hc and halocidin to Gram negative bacteria such as *Pseudomonas aeruginosa, Salmonella cholerasuis, Salmonella parotyphi* A, *E. coli* K112 and *E. coli* DH5α. At that time, used buforin 2 and magainin 1 for comparative group.

As a result, 15Hc and 18Hc hardly showed or had minimum antimicrobial activity even though the concentration of peptide increased. However, halocidin showed almost the same level of antimicrobial activity as magainin 1 and buforin 2, which were the comparative group, or higher antimicrobial activity than comparative group according to the kinds of bacteria (FIG. 12).

The present inventors performed radical diffusion assay again for (18-1)Hc, di-(18-1)Hc, 18Hc and di-18Hc with the same method as the above. As a result, di-(18-1)Hc and di-18Hc, which were in dimer form, showed higher antimicrobial activity than (18-1)Hc and 18Hc, which were in monomer forms, though it varied upon the kinds of bacteria (FIG. 13).

The present inventors performed radical diffusion assay for (18-2)Hc, di-(18-2)Hc, (18)Hck and di-(18)Hck with the same method as the above. As a result, di-(18-2)Hc and di-(18)Hck, which were in dimer forms, showed higher antimicrobial activity than (18-2)Hc and (18)Hck, which were in monomer forms (FIG. 14).

Based on the above results, the present inventors confirmed that halocidin had high antimicrobial activity to Gram-negative bacteria and showed the highest activity when monomers, subunits of halocidin, were in dimer forms.

<3-5> Comparing Antimicrobial Activity to Gram Positive Bacteria

The present inventors investigated the antimicrobial activity of halocidin to Gram-positive bacteria. Particularly, performed radical diffusion assay with the same method as the above Example 1 to confirm the antimicrobial activity of each 15Hc, 18Hc, halocidin, buforin 2 and magainin 1 to Gram-positive bacteria such as *Staphylococcus aureus, Micrococcus luteus, Enterococcus faecalis, Bacillus subtilus* and MRSA.

As a result, just halocidin showed high antimicrobial activity. 15Hc and 18Hc were proved to have low antimicrobial activity (FIG. 15).

The present inventors performed radical diffusion assay again for (18-1)Hc, di-(18-1)Hc, 18Hc and di-18Hc with the same method as the above. As a result, di-(18-1)Hc and di-18Hc, which were in dimer forms, showed higher antimicrobial activity than (18-1)Hc and 18Hc, which were in monomer forms, though it varied upon the kinds of bacteria (FIG. 16).

The present inventors performed radical diffusion assay for (18-2)Hc, di-(18-2)Hc, (18)Hck and di-(18)Hck with the same method as the above. As a result, di-(18-2)Hc and di-(18)Hck, which were in dimer forms, showed higher antimicrobial activity than (18-2)Hc and (18)Hck, which were in monomer forms (FIG. 17).

Based on the above results, the present inventors confirmed that halocidin had high antimicrobial activity to Gram-positive bacteria and showed the highest activity when monomers, subunits of halocidin, were in dimer forms.

<3-6> Antimicrobial Activity According to pH

In order to confirm if halocidin having high antimicrobial activity to bacteria still keeps the activity under the low pH condition in vivo, the present inventors investigated the change of antimicrobial activity according to pH by radical diffusion assay. Particularly, adjusted the pH of media to 7.4, 6.5 and 5.5 respectively by adding HCl, which was checked with a pH meter, and performed radical diffusion assay with the same method as the above Example 1 to investigate the antimicrobial activity to MRSA and *Enterococcus faecalis*.

As a result, it was confirmed that di-18Hc, di-(18-1)Hc and di-k(18+1)Hc kept the same antimicrobial activity even under low pH condition, pH 5.5, which was similar condition to the environment of epithelial tissue, urethra, intravagina, etc, as that under pH 7.4(Table 4).

TABLE 4

|  | Peptide | MRSA | Enterococcus faecalis |
|---|---|---|---|
| pH = 7.4 | Halocidin | >64 | >64 |
|  | K(18 + 1)Hc | 16-32 | 8-16 |
|  | di-(18 − 1)Hc | 8-16 | 8-16 |
|  | di-18Hc | 8-16 | 2-4 |
|  | di-K(18 + 1)Hc | 2-4 | 2-4 |
|  | P18 | 8-16 | 32-64 |
|  | Magainin 1 | >64 | >64 |
|  | Buforin 2 | >64 | >64 |
|  | Secrofin A | >64 | >64 |
| pH = 6.5 | Halocidin | >64 | >64 |
|  | K(18 + 1)Hc | 16-32 | 16-32 |
|  | di-(18 − 1)Hc | 2-4 | 4-8 |
|  | di-18Hc | 2-4 | 4-8 |
|  | di-K(18 + 1)Hc | 2-4 | 2-4 |
|  | P18 | 32-64 | >64 |
|  | Magainin 1 | >64 | >64 |
|  | Buforin 2 | >64 | >64 |
|  | Secrofin A | >64 | >64 |
| pH = 5.5 | Halocidin | >64 | >64 |
|  | K(18 + 1)Hc | 32-64 | 16-32 |
|  | di-(18 − 1)Hc | 8-16 | 2-4 |
|  | di-18Hc | 4-8 | 2-4 |
|  | di-K(18 + 1)Hc | 2-4 | 2-4 |
|  | P18 | >64 | >64 |
|  | Magainin 1 | >64 | >64 |
|  | Buforin 2 | >64 | >64 |
|  | Secrofin A | >64 | >64 |

<3-7> Antimicrobial Activity According to Base

The present inventors confirmed if halocidin still had antimicrobial activity under the strong basic condition in vivo. Particularly, changed the basic condition of media by adding 100 mM NaCl, 150 mM NaCl and 200 mM NaCl respectively, and investigated the antimicrobial activity to MRSA and *Enterococcus faecalis* by radical diffusion assay.

As a result, it was confirmed that di-18Hc, di-(18-1)Hc and di-k(18+1)Hc kept the same antimicrobial activity even under strong basic condition (200 mM) as that under non-basic condition (Table 5).

TABLE 5

|  | Peptide | MRSA | Enterococcus faecalis |
|---|---|---|---|
| NaCl 100 mM | Halocidin | >64 | >64 |
|  | K(18 + 1)Hc | 16-32 | 16-32 |
|  | di-(18 − 1)Hc | 4-8 | 8-16 |
|  | di-18Hc | 8-16 | 2-4 |
|  | di-K(18 + 1)Hc | 4-8 | 2-4 |
|  | P18 | >64 | >64 |
|  | Magainin 1 | >64 | >64 |
|  | Buforin 2 | >64 | >64 |
|  | Secrofin A | >64 | >64 |
| NaCl 150 mM | Halocidin | >64 | >64 |
|  | K(18 + 1)Hc | 16-32 | 16-32 |
|  | di-(18 − 1)Hc | 8-16 | 8-16 |
|  | di-18Hc | 8-16 | 2-4 |
|  | di-K(18 + 1)Hc | 4-8 | 2-4 |
|  | P18 | >64 | >64 |
|  | Magainin 1 | >64 | >64 |
|  | Buforin 2 | >64 | >64 |

TABLE 5-continued

| | Peptide | MRSA | Enterococcus faecalis |
|---|---|---|---|
| | Secrofin A | >64 | >64 |
| NaCl | Halocidin | >64 | >64 |
| 200 mM | K(18 + 1)Hc | 32-64 | 16-32 |
| | di-(18 − 1)Hc | 8-16 | 8-16 |
| | di-18Hc | 16-32 | 2-4 |
| | di-K(18 + 1)Hc | 4-8 | 2-4 |
| | P18 | >64 | >64 |
| | Magainin 1 | >64 | >64 |
| | Buforin 2 | >64 | >64 |
| | Secrofin A | >64 | >64 |

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A peptide separated from tunicate and comprising amino acid sequence represented by chemical formula I:

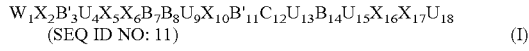

$$W_1X_2B'_3U_4X_5X_6B_7B_8U_9X_{10}B'_{11}C_{12}U_{13}B_{14}U_{15}X_{16}X_{17}U_{18} \quad (I)$$
(SEQ ID NO: 11)

wherein,

W represents tryptophan;

X, each variable of which $X_2$, $X_5$, $X_6$, $X_{10}$, $X_{16}$ and $X_{17}$ is individually selected from an amino acid residue selected from the group consisting of tyrosine, valine, isoleucine, leucine, methionine, phenylalanine and tryptophan;

B represents an amino acid residue selected from the group consisting of arginine, lysine and histidine;

B' represents an amino acid residue selected from the group consisting of arginine, lysine and histidine or from a group consisting of asparagine and glutamine;

C is Cysteine;

U represents an amino acid residue selected from the group consisting of glycine, serine, alanine and threonine.

2. The peptide as set forth in claim 1, wherein the tunicate is *Halocynthia aurantium*.

3. The peptide as set forth in claim 1, wherein the peptide comprises amino acid sequence SEQ. ID No: 1.

4. A peptide comprising an amino acid sequence represented by chemical formula II:

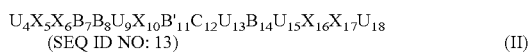

$$U_4X_5X_6B_7B_8U_9X_{10}B'_{11}C_{12}U_{13}B_{14}U_{15}X_{16}X_{17}U_{18} \quad (II)$$
(SEQ ID NO: 13)

wherein,

U represents an amino acid residue selected from a group consisting of glycine, serine, alanine and threonine;

X, each variable of which $X_5$, $X_6$, $X_{10}$, $X_{16}$ and $X_{17}$ is individually selected from an amino acid residue selected from the group consisting of tyrosine, valine, isoleucine, leucine, methionine, phenylalanine and tryptophan;

B represents an amino acid residue selected from the group consisting of arginine, lysine and histidine; and B' represents an amino acid residue selected from the group consisting of arginine, lysine and histidine or from a group consisting of asparagine and glutamine.

5. The peptide as set forth in claim 4, wherein the peptide comprises an amino acid sequence represented by SEQ ID NO: 15 in which $U_4$ is alanine, $X_5$ is leucine, $X_6$ is leucine, $B_7$ is histidine, $B_8$ is histidine, $U_9$ is glycine, $X_{10}$ is leucine, $B'_{11}$ is asparagine, $C_{12}$ is cysteine, $U_{13}$ is alanine, $B_{14}$ is lysine, $U_{15}$ is glycine, $X_{16}$ is valine, $X_{17}$ is leucine and $U_{18}$ is alanine.

6. A peptide dimer comprising an amino acid sequence represented by chemical formula III: wherein each peptide of the dimer is represented by chemical formula I (SEQ ID NO: 11) and the peptides are joined at the cysteine site by disulfide bond;

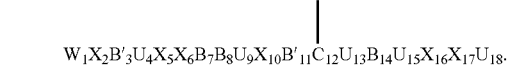

$$W_1X_2B'_3U_4X_5X_6B_7B_8U_9X_{10}B'_{11}C_{12}U_{13}B_{14}U_{15}X_{16}X_{17}U_{18} \quad (III)$$
$$|$$
$$W_1X_2B'_3U_4X_5X_6B_7B_8U_9X_{10}B'_{11}C_{12}U_{13}B_{14}U_{15}X_{16}X_{17}U_{18}.$$

7. A peptide dimer comprising an amino acid sequence represented by formula IV: wherein each peptide of the dimer is represented by chemical formula II (SEQ ID NO: 13), and the peptides are joined at the cysteine site by disulfide bond;

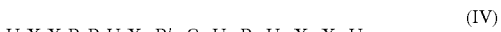
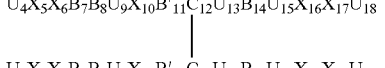

$$U_4X_5X_6B_7B_8U_9X_{10}B'_{11}C_{12}U_{13}B_{14}U_{15}X_{16}X_{17}U_{18} \quad (IV)$$
$$|$$
$$U_4X_5X_6B_7B_8U_9X_{10}B'_{11}C_{12}U_{13}B_{14}U_{15}X_{16}X_{17}U_{18}.$$

8. A peptide dimer comprising an amino acid sequence represented by formula V: wherein one peptide of the dimer is represented by chemical formula I (SEQ ID NO: 11) and another peptide of the dimer is represented by chemical formula II (SEQ ID NO: 13), and the peptides are joined at the cysteine site by disulfide bond;

$$W_1X_2B'_3U_4X_5X_6B_7B_8U_9X_{10}B'_{11}C_{12}U_{13}B_{14}U_{15}X_{16}X_{17}U_{18} \atop \phantom{W_1X_2B'_3}U_4X_5X_6B_7B_8U_9X_{10}B'_{11}C_{12}U_{13}B_{14}U_{15}X_{16}X_{17}U_{18}.} \quad (V)$$

9. An antimicrobial agent comprising a peptide comprising the chemical formula I of claim 1 as an active ingredient.

10. An antimicrobial agent comprising a peptide comprising the chemical formula II of claim 4 as an active ingredient.

11. An antimicrobial agent comprising a peptide dimer comprising the chemical formula III of claim 6 as an active ingredient.

12. An antimicrobial agent comprising a peptide dimer comprising the chemical formula IV of claim 7 as an active ingredient.

13. An antimicrobial agent comprising a peptide dimer comprising the chemical formula V of claim 8 as an active ingredient.

* * * * *